United States Patent [19]

Bihovsky et al.

[11] Patent Number: 5,504,070
[45] Date of Patent: Apr. 2, 1996

[54] INHIBITORS OF THE CONVERSION OF BIG ENDOTHELIN TO ENDOTHELIN

[75] Inventors: Ron H. Bihovsky, Convent Station; Paul W. Erhardt, Long Valley; John W. Lampe, Rockaway; Raju Mohan, Randolph; Kenneth J. Shaw, Califon, all of N.J.

[73] Assignee: Berlex Laboratories, Inc., Wayne, N.J.

[21] Appl. No.: 802,667

[22] Filed: Dec. 5, 1991

[51] Int. Cl.⁶ .............................. A61K 38/00; C07K 5/06; C07K 7/06; C07K 7/00
[52] U.S. Cl. ................. 514/15; 514/16; 514/19; 530/328; 530/329
[58] Field of Search .................. 514/16–19, 15; 530/329, 328

[56] References Cited

U.S. PATENT DOCUMENTS

| | | |
|---|---|---|
| 4,452,790 | 6/1984 | Karanewsky . |
| 4,610,816 | 9/1986 | Berger .................................. 549/452 |
| 4,918,105 | 4/1990 | Cartwright . |

FOREIGN PATENT DOCUMENTS

| | | |
|---|---|---|
| 249445 | of 0000 | European Pat. Off. . |
| 320118 | of 0000 | European Pat. Off. . |
| 0209897 | 1/1987 | European Pat. Off. . |
| 0306879 | 3/1989 | European Pat. Off. . |
| 58-124794 | of 0000 | Japan . |

*Primary Examiner*—Jill Warden
*Assistant Examiner*—S. G. Marshall
*Attorney, Agent, or Firm*—Elizabeth A. Bellamy; Diana Hamlet-King; Richard M. Lebovitz

[57] ABSTRACT

Novel and known compounds are described which inhibit endothelin converting enzyme (ECE), thereby preventing the conversion of Big Endothelin (BET) to Endothelin (ET). Pharmaceutical usefulness and preparations are described.

71 Claims, No Drawings

INHIBITORS OF THE CONVERSION OF BIG ENDOTHELIN TO ENDOTHELIN

This invention relates to compounds which are useful in inhibiting the conversion of Big Endothelin (BET) to Endothelin (ET). That is, compounds useful when abnormal levels of endothelin are associated with pathophysiologic states. Elevated endothelin levels have been implicated in, for instance, vascular spasm and ischemia as well as cardiac, renal, CNS, vasculative and bronchial disease mates.

General Description of the Invention

Composition-of-Matter Aspect

This invention relates to known and novel compounds which are useful as inhibitors of the conversion of BET to ET. The compounds, both known and novel, which inhibit the conversion of BET to ET are of the following formulae I–VI.

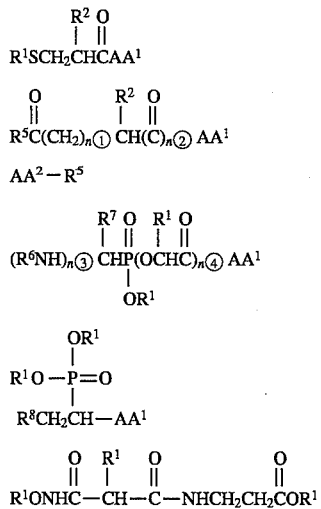

$R^1$ is H, alkyl, cycloalkyl, cycloalkylalkyl, phenyl, aralkyl.

$R^2$ is H, alkyl, phenyl, aralkyl, (3-indolyl)methylene, $NHR^3$.

$AA^1$ is $OR^1$, $NH_2$, Val-$OR^1$, Val-$NH_2$, Val-Asn-$OR^1$, Val-Asn-$NH_2$, Val-β-Ala-$NH_2$, Val-β-Ala-$OR^1$, Val-Asn-Thr-$OR^1$, Val-Asn-Thr-Pro-$OR^1$(SEQ ID NO: 1), Val-Asn-Thr-Pro-Glu-$NH_2$(SEQ ID No: 2), Asn-$OR^1$, Asn-$NH_2$, Asn-Thr-$OR^1$, Asn-Thr-Pro-$OR^1$, Asn-Thr-Pro-Glu-$NH_2$(SEQ ID No: 3), β-Ala-$OR^1$, β-Ala-$NHR^1$, Trp-$OR^1$, Trp-$NH_2$, Trp-β-Ala-$OR^1$, Trp-NH-$R^1$.

$R^3$ is H, acetyl, benzoyl, $AA^2$.

$AA^2$ is $R^4$-Trp, $R^4$-Ile-Trp, $R^4$-Ile-Ile-Trp, $R^4$-Asp-Ile-Ile-Trp (SEQ ID No: 4), $R^4$—($OR^1$)Asp-Ile-Ile-Trp (SEQ ID No: 5), with the proviso that in formula III $AA^2$ must be at least three amino acids in length.

$R^4$ is H, acetyl, benzoyl, carbobenzyloxy ("Z"), t-butoxycarbonyl ("BOC").

$R^5$ is $OR^1$, $NHOR^1$.

n① is 0, 1, 2.

n② is 0, 1 and when in formula II $R^2$=$NHR^3$, n② cannot be zero.

n③=0,1 and when absent it is replaced by H.

n④=0,1.

$R^6$ is $R^4$, $AA^2$, $R^4$-Ile, $R^4$-Ile-Ile, $R^4$-Asp-Ile-Ile, $R^4$-($OR^1$)Asp-Ile-Ile.

$R^7$ is $R^1$, (3-indolyl)methylene.

$R^8$ is $R^7$, $NHR^6$.

The novel compounds of this invention are those defined by the following formulae I, II and VI. Those novel compounds defined by formula I are as follows:

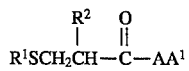

wherein $R^1$ is H, alkyl, cycloalkyl, cycloalkylalkyl, phenyl, aralkyl.

$R^2$ is $NHR^3$.

$AA^1$ is $OR^1$, $NH_2$, Val-$OR^1$, Val-$NH_2$, Val-Asn-$OR^1$, Val-Asn-$NH_2$, Val-β-Ala-$NH_2$, Val-β-Ala-$OR^1$, Val-Asn-Thr-$OR^1$, Val-Asn-Thr-Pro-$OR^1$, (SEQ ID No: 1), Val-Asn-Thr-Pm-Glu-$NH_2$(SEQ ID No: 2), Asn-$OR^1$, Asn-$NH_2$, Asn-Thr-$OR^1$, Asn-Thr-Pro-$OR^1$, Asn-Thr-Pro-Glu-$NH_2$(SEQ ID No: 3), β-Ala-$OR^1$, β-Ala-$NHR^1$, Trp-$OR^1$, Trp-$NH_2$, Trp-β-Ala-$OR^1$, Trp-NH-$R^1$.

$R^3$ is $AA^2$.

$AA^2$ is $R_4$-Trp, $R^4$-Ile-Trp, $R^4$-Ile-Ile-Trp (SEQ ID No: 4), $R^4$-Asp-Ile-Ile-TrP, $R^4$—($OR^1$) Asp-Ile-Ile-Trp (SEQ ID No: 5), with the proviso that when $AA^1$ is $OR^1$ or $NH_2$ then $AA^2$ must be at least 3 amino acids.

$R^4$ is H, acetyl, benzoyl, carbobenzyloxy ("Z"), t-butoxycarbonyl ("BOC").

and the pharmaceutically acceptable salts thereof.

Those novel compounds defined by formula II are as follows:

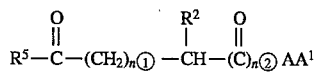

wherein:

$R^1$ is H, alkyl, cycloalkyl, cycloalkylalkyl, phenyl, arlkyl.

$R^2$ is $NHR^3$.

$AA^1$ is Val-$OR^1$, Val-$NH_2$, Val-Asn-$OR^1$, Val-Asn-$NH_2$, Val-β-Ala-$NH_2$, Val-β-Ala-$OR^1$, Val-Asn-Thr-$OR^1$, Val-Asn-Thr-Pro-$OR^1$(SEQ ID No: 1), Val-Asn-Thr-Pro-Glu-$NH_2$(SEQ ID No: 2), Asn-$OR^1$, Asn-$NH_2$, Asn-Thr-$OR^1$, Asn-Thr-Pro-$OR^1$, Asn-Thr-Pro-Glu-$NH_2$(SEQ ID No: 3), β-Ala-OR $^1$, β-Ala-$NHR^1$, Trp-$OR^1$, Trp-$NH_2$, Trp-β-Ala-$OR^1$, Trp-NH-$R^1$.

$R^3$ is $AA^2$.

$AA^2$ is $R_4$-Trp, $R^4$-Ile-Trp, $R^4$-Ile-Ile-Trp, $R^4$-Asp-Ile-Ile-Trp (SEQ ID No: 4), $R^4$—($OR^1$)Asp-Ile-Ile-Trp (SEQ ID No: 5).

$R^4$ is H, acetyl, benzoyl, carbobenzyloxy ("Z"), t-butoxycarbonyl ("BOC").

$R^5$ is $OR^1$, $NHOR^1$.

n① is 0, 1, 2.

n② >is 1.

and the pharmaceutically acceptable salts thereof.

Those novel compounds defined by Formula VI are as follows:

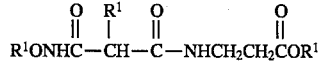

wherein:

R¹ is H, alkyl, cycloalkyl, cycloalkylalkyl, phenyl or aralkyl, and the pharmaceutically acceptable salts thereof.

The pharmaceutically acceptable salts contemplated as part of this invention include inorganic acids such as hydrobromic, hydrochloric, sulfuric, phosphoric and organic acids such as acetic, propanoic, benzoic, naphthalenecarboxylic, succinic, malic, adipic, lactic, tartaric, citric, salicylic, methanesulfonic and p-toluenesulfonic. Also included are those utilizing the alkaline earth metals such as lithium, potassium and sodium.

It is to be understood that the definition of the compounds of Formulae I–VI encompasses all possible stereoisomers and mixtures thereof which possess the activity discussed below. In particular, it encompasses racemic modifications and any optical isomers which possess the individual activity.

It is also understood that the definition of the compounds of Formula I–VI encompasses all possible polymorphic modifications and other solid state modifications which possess the stated activity.

In the foregoing formulae I–VI the term alkyl refers to a straight or branched chain of 1 to 10 carbon atoms and shall be inclusive of but not limited to methyl, ethyl, propyl, isopropyl, butyl, isobutyl, tertiary butyl, sec. butyl, pentyl, isopentyl, hexyl, 3-methylpentyl, heptyl, 2-methylhexyl, octyl and 2-ethylhexyl, nonyl and decyl.

The term cycloalkyl shall refer to a saturated carbocyclic ring containing 5 or 6 carbon atoms whilst a cycloalkylalkyl shall refer to a saturated carbocyclic ring containing 5 or 6 carbon atoms attached to a straight or branched alkyl chain containing up to 9 carbon atoms. The term aralkyl shall refer to a phenyl ring on a straight or branched alkyl chain containing from 1–9 carbon atoms.

The compounds which follow are some of those which serve to exemplify various aspects of the invention described herein.

1. N-Benzoyl-L-cysteinyl-L-valyl-L-asparagine.
2. N-Benzoyl-L-cysteinyl-L-valyl-β-alanine.
3. N-[(2-Mercaptomethyl-3-methyl-l-oxo)butyl]-β-alanine.
4. N-[N-[3-(1-Indol-3-yl)-2-(mercaptomethyl)-1-oxopropyl]-L-valyl]-L-asparagine.
5. N-[N-[3-(1-Indol-3-yl)-2-(mercaptomethyl)-1-oxopropyl]-L-valyl]-β-alanine.
6. N-Benzoyl-L-α-glutamyl-L-valyl-β-alanine.
7. N-Benzoyl-L-α-aspartyl-L-valyl-β-alanine.
8. N-Benzoyl-N-hydroxy-L-glutaminyl-L-valyl-L-aspartamide.
9. N-Benzoyl-N-hydmxy-L-asparaginyl-L-valyl-L-aspartamide.
10. N-Acetyl-L-isoleucyl-L-isoleucyl-L-tryptophyl-L-α-glutamine (SEQ ID No: 6).
11. N-Acetyl-L-isoleucyl-L-isoleucyl-L-tryptophyl-L-asparagine (SEQ ID No: 7).
12. N-Acetyl-L-isoleucyl-L-isoleucyl-L-tryptophyl-$N_5$-hydroxy-L-glutamide (SEQ ID No: 8).
13. N-Acetyl-L-isoleucyl-L-isoleucyl-L-tryptophyl-$N_4$-hydroxy-L-aspartamide (SEQ ID No: 9).
14. N-Acetyl-L-isoleucyl-L-isoleucyl-L-tryptophyl-$N_1$-(2-methylethyl)-L-α-glutamine (SEQ ID No: 10).
15. N-Acetyl-L-isoleucyl-L-isoleucyl-L-tryptoPhyl-$N_1$-hydroxy-glutaminylanide (SEQ ID No: 11).
16. N-Acetyl-L-isoleucyl-L-isoleucyl-L-tryptophyl-$N_1$-(2-methylethyl)-L-aspartamide (SEQ ID No: 12).
17. N-Acetyl-L-isoleucyl-L-isoleucyl-L-tryptophyl-$N_4$-hydroxy-$N_1$-( 2-meth ylethyl)-L-asparaginylamide (SEQ ID NO: 13).
18. N-Acetyl-L-isoleucyl-L-isoleucyl-N-hydroxy-L-tryptophanamide.
19. L-Isoleucyl-L-isoleucyl-N-hydroxy-L-tryptophanamide.
20. N-[2-[[Hydroxy(3-phenylpropyl)phosphinyl]oxy]-1-oxopropyl]-β-alanine.
21. N-[2-[[Hydroxy(3-phenylpropyl)phosphinyl]oxy]-3-(1H-indol- 3-yl)oxopropyl]-L-asparagine.
22. N-[2-[[[1-[N-Acetyl-L-isoleucyl-L-isoleucyl)amino]-2-phenylethyl]hydroxyphosphinyl]oxy]-3-methyl-1-oxobutyl]-L-asparagine.
23. N-[2-[[[1-[N-(N-Acetyl-L-isoleucyl-L-isoleucyl)amino]-2-(1H-indol-3-yl)ethyl]hydroxyphosphinyl] oxy]-3-methyl-1-oxobutyl]-β-alanine.
24. N-[N-[1-[[N-(N-Acetyl-L-isoleucyl-L-isoleucyl)amino]-2-(1H-indol-3-yl)ethyl]hydroxphosphinyl] oxy]-L-valyl]-L-asparagine.
25. N-[N-[[1-[(N-Acetyl-L-isoleucyl-L-isoleucyl)amino]-2-(1 H-indol- 3yl)ethyl]hydroxyphosphinyl]-L-valyl-L-β-alanine.
26. N-[N-I[[2-[(N-Acetyl-L-isoleucyl-L-isoleucyl)amino] 1-dihydroxy-phosphinyl]ethyl]-L-valyl]-L-asparagine.
27. N-[N-[[2-[(N-Acetyl-L-isoleucyl-L-isoleucyl]amino] 1-dihydroxy-phosphinyl]ethyl]-L-valyl]-β-alanine.

PROCESS ASPECT

The compounds described in this invention can be prepared by standard techniques known to those skilled in the chemistry of amino acids, their derivatives and peptides. Suggested procedures for synthesis of these compounds are described below.

Amide bonds in the following examples are generally prepared by condensations between carboxylic acids and amines. Reagents capable of effecting this condensation include, but are not limited to, oxalyl chloride, thionyl chloride, phosphoryl chloride, diarylphosphoryl azides, diarylphosphoryl cyanide, and carbodiimides. Carbodiimides may be utilized in conjunction with 1-hydroxybenzotriazole, N-hydroxysuccinimide, and other reagents well known in the synthesis of peptides. Salts of the described carboxylic acids may generally be used in place of the carboxylic acids. Likewise, salts of the described amines may frequently be used in place of the amines.

In some examples, alkyl and aralkyl esters have been utilized to protect carboxylic acids, hydroxamic acids, and phosphonic acids. The protecting group can be removed by well established procedures. Thus t-butyl esters can be hydrolyzed by mineral or organic acids such as HCl, HBr, or trifluoroacetic acid. Primary alkyl esters can be hydrolyzed with base. Benzyl esters can also be removed by hydrogenation. Various peptides can be prepared by manual or automated solid phase peptide synthesis, the latter utilizing instruments such as a MilliGen Model 9050 continuous-flow synthesizer.

Still further, the references which follow may be utilized for the preparation of some of the compounds of this invention. EP 231,081 published Jun. 5, 1987; EP 75,896 published Apr. 6, 1983; WO 90/05716 published May 31, 1990; EP 97,534 published Jun., 1983; Karnewsky, et al. J. Med. Chem. (1988) 31,204–212; Elliot, et al. J. Med. Chem. (1985) 28, 1208–1216; Rogues et al. Nature, (1980) 288, 286–288 and Fournie-Zaluski, et al. J. Med. Chem. (1983) 26, 60–65.

Method-of-Use and Pharmaceutical Composition Aspect

The compounds described herein have been found to be inhibitors of the conversion of Big Endothelin (BET) to Endothelin (ET). Thus, it is contemplated that these compounds would be useful in alleviating those disease states where abnormal levels of endothelin contribute to the pathophysiology.

Endothelial cells produce endothelin, a 21 residue polypeptide which is an extremely potent vasoconstdctor—more powerful even than angiotensin II. It is thought that endothelin is produced by cleavage of the bond linking the residues Trp 21- Val 22 in the immediate precursor, BET. This cleavage which produces ET from BET is accomplished by a hitherto unidentified endo-peptidase known as endothelin converting enzyme (ECE).

Thus, it is ECE that the compounds of this invention inhibit thereby preventing the conversion of BET to ET. Heretofore, ECE was an unidentified endopeptidase—U.S. Ser.No. 650,394 filed Feb. 4, 1991 is now incorporated herein in its entirety. In this application—ECE is identified and purified and thus can be utilized to measure the inhibitory effect of the peptides of this invention. It is understood that ECE produced from another source via another method of purification can be utilized.

ET is a potent vasoconstrictor in both arterial and venous beds and as stated above it is likely that abnormal levels of endothelin contribute directly to the pathophysiology in a number of disease states.

For example, high circulating levels of ET have been found in patients with congestive heart failure, advanced atherosclerotic disease, essential, malignant and transplant hypertension, pre-eclampsia and renal dysfunction. Underwood, et al.—Heart Failure—April/May 1991, 50–58; Naylor, TIPS—March 1990 [Vol. II], 96–99 and Yorikane, et al. Bioch. & Biophys. Res. Comm., Vol. 173, Nov. 30, 1990, 457–462 and Bock et al. J. Clin. Invest. 83: 336–342 (1989); Predal et al. Life Sciences 47, 1837 (1990); Yanagisawa et al., Nature 332, 411–415 (1988); Asano et al. BBRC 15, 1345–1351 (1989); Mayzi et al. Eur. J. Pharmacol. 160:179–182 (1989); Clozel & Clozel. Circ. Res. 65, 1193–1200 (1989) discuss at length the vadous disease states wherein levels of endothelin—usually excessive—have been implicated. In addition, measurement of the direct action of ET in a number of animal models show that lowering its concentration would be useful in the following settings: various vasospastic and ischemic diseases such as angina, myocardial infarction, stroke, cardiac arrhythmias, and renal ischemic dysfunction. Thus, the diagnosis and/or treatment of these disease states could be treated by the administration of these ECE inhibitors.

The ECE inhibition of the compounds of this invention are measured in the following manner. Potential inhibitors of ECE are initially screened in duplicate incubations at a concentration of 10 uM. The test compound is dissolved in DMSO and added to the assay mixture such that the final concentration of DMSO is 1% (v/v). The assay mixture also contains 50 mM MOPS buffer, pH 7.2, 150 mM NaCl, 30 µM $CaCl_2$, 2.5 mM β-octylglucoside, 1 µM amastatin, 1 mM PMSF, and sufficient ECE (purified from the 100,000×g membrane fraction of human bronchiolar smooth muscle cells) to produce 1–3 pmol ET-1 per hr at 37° C. in the absence of added inhibitor. Following a 30 minute preincubation at room temperature, the reaction is initiated by the addition of human BET-1 to a final concentration of 3 uM. After incubation for 4 hr at 37° C., the reaction is quenched by the addition of 3 mM EDTA, pH 7.0. The product, ET-1, is separated from the substrate, hBET-1, by reverse phase HPLC on a $C_{18}$ column, and quantitated by comparing its tryptophan fluorescence to known amounts of authentic ET-1 chromatographed under the same conditions.

Compounds found to inhibit ECE activity more than 50% at a concentration of 10 uM are evaluated in duplicate at a minimum of 3 concentrations in order to determine an $IC_{50}$ value.

The compounds of the invention as for instance N-[2-[(hydroxyamino)carbonyl] 3-methyl-1-oxobutyl]-β-alanine will be administered in accordance with the disease state where the level of endothelin is implicated. In general, the compounds will be administered orally or parenterally. The dosage and method of administration will be dependent on the nature of the compound to be administered as well as the age, weight, sex and other characteristics of the subject to be treated and the disease state to be diagnosed and/or treated. The compounds when administered orally or parenterally will be admixed with pharmaceutically acceptable carriers in accordance with standard pharmaceutical practices, taking into account the amount and type of compound to be administered, its dosage form and the disease state it is to affect.

It is also contemplated that the compounds can be used in a kit-format for the identification/standardization of future ECE inhibitors. The inhibitors can also be used as a probe to determine whether ECE is in the sample.

The invention described hereinabove is illustrated below in the Examples, which, however, are not to be construed as limiting the invention.

EXAMPLES

The following abbreviations are those used in the Examples.

| | |
|---|---|
| Fmoc | 9-Fluorenylmethoxycarbonyl- |
| t-Boc | t-Butyloxycarbonyl- |
| OPfp | Pentafluorophenoxy |
| ODhbt | 3,4-Dihydro-4-oxo-benzotriazine-3-oxy |
| BOP | Benzotriazolyloxy-trisdimethylaminophosphonium hexafluorophosphate |
| HOBt | 1-Hydroxybenzotriazole |
| DMF | N,N-Dimethylformamide |
| TFA | Trifluoroacetic acid |
| HF | Hydrogen fluoride |
| PAM | Phenylacetamidomethyl |
| MBHA | p-Methylbenzhydrylamine |
| Bzl | Benzyl |
| Tos | p-Toluenesulfonyl |
| HOSu | N-Hydroxysuccinimide |
| EDC | 1-Ethyl-3-(3-Dimethylaminopropyl)-Carbodiimide HCl |
| OSu | Succinimidoxy |
| Cbz | Benzyloxycarbonyl |
| DCC | Dicyclohexylcarbodiimide |

PROCEDURE A

Protected peptides are synthesized on a MilliGen Model 9050 continuous-flow synthesizer using Fmoc-based chemistry and either active ester (OPfp or ODhbt esters) or BOP/HOBt coupling protocols as specified by the instrument manufacturer. The side chains of Asp and Glu are protected as t-butyl esters; the side chain of Thr is protected as the t-butyl ether. Cysteine is protected as the S-tdtyl derivative. AminoTech PR$^{500}$ resin (a resin for continuous flow synthesis of peptide amides based on a Polyhipe matrix functionalized with norleucine and a modified Rink linker) is purchased from AminoTech with a substitution level of 0.43 mmole/g. The 1.0 synthesis scale is adjusted to take into account the higher loading of the PolyHIPE based resins; the flow rate used is 10 mL/min. The first amino acid is double-coupled to the resin. Coupling cycles are extended in the case of couplings involving lle, Val, and Pro, and when the chain length exceeds 6 residues. Acetylation is carried out on-line with 0.5M acetic anhydride/0.5M pyridine in DMF, followed by DMF and DCM washes. The peptides are cleaved from the dried resin by portionwise treatment with 95:5 TFN water. Tryptophan is added to the cleavage mixture as a scavenger in cases where a Trp residue is present. Crude peptides are isolated by precipitation into diethyl ether (250 mL). Purification is effected either by trituration with water to remove water-soluble contaminants, or by preparative HPLC on a Vydac C-18 (10 µL) column using a gradient of acetonitrile/0.1% TFA (10–80% acetonitrile over 2 hr).

EXAMPLE 1

N-Acetyl-L-α-aspartyl-L-valyl-L-asparaginyl-L-threonyl-L-prolyl-L-α-glutamine (SEQ ID NO:14)

According to Procedure A, 1.0 g (0.43 mmole) AminoTech PR500 resin is preswelled in DMF and packed into a standard MilliGen 9050 reaction column. Fmoc-L-Glu(O-t-Bu)-OPfp (1.017 g, 1.72 mmole) is doubled coupled to the resin. Subsequent couplings of Fmoc-L-Pro-OPfp (0.868 g, 1.72 mmole), Fmoc-L-Thr(t-Bu)-ODhbt (0.933 g, 1.72 mmole), Fmoc-L-Asn-OPfp (0.895 g, 1.72 mmole, Fmoc-L-Val-OPfp (0.869 g, 1.72 mmole), and Fmoc-L-Asp(O-t-Bu)-OH (0.993 g, 1.72 mmole) are carried out. Acetylation is accomplished with 0.5M acetic anhydride/0.5M pyridine in DMF (150 mL). The peptide-resin is cleaved by two treatments with 95:5 TFA/water (10 mL/15 min and 10 mL/60 min) and precipitation into diethyl ether. Lyophilization from water yields the title compound. FAB MS: (M+H)$^+$ :715 AAA: Asx 1.80(2); Glx 0.89(1); Thr 1.01(1); Val 1.00(1) HPLC: 95.7% (Area %).

EXAMPLE 2

In a manner similar to Example 1, the following compounds may be prepared:
  a)   N-Acetyl-L-α-glutamyl-L-valyl-L-asparaginyl-L-threonyl-L-prolyl-L-α-glutamine (SEQ ID NO: 15).
  b)   N-N-Acetyl-L-cysteinyl-L-valyl-L-asparaginyl-L-threonyl-L-prolyl-L-α-glutamine (SEQ ID NO: 16).

EXAMPLE 3

In a manner similar to Example 1, cleaving the peptide from the resin with 20 mL of a mixture of TFA/water (90:10) +120 mg tryptophan (in two portions), the following compounds may be prepared:
  a)   N-Acetyl-L-α-aspartyl-L-isoleucyl-L-isoleucyl-L-tryptophyl-L-α -glutamyl-L-valyl-L-asparaginyl-L-threonyl-L-pmlyl-L-α-glutamine (SEQ ID NO: 17).
  b)   N-Acetyl-L-α-aspartyl-L-isoleucyl-L-isoleucyl-L-tryptophyl-L-α-aspartyl-L-valyl-L-asparaginyl-L-threonyl-L-prolyl-L-α-glutamine (SEQ ID NO: 18).
  c)   N-Acetyl-L-α-aspartyl-L-isoleucyl-L-isoleucyl-L-tryptophyl-L-α-aspartamide (SEQ ID NO: 19).
  d)   N-N-Acetyl-L-α-aspartyl-L-isoleucyl-L-isoleucyl-L-tryptophyl-L-α-glutamine (SEQ ID NO: 20).
  e)   N-Acetyl-L-α-aspartyl-L-isoleucyl-L-isoleucyl-L-tryptophyl-L-cysteinamide (SEQ ID NO: 21).

EXAMPLE 4

N-Acetyl-L-α-aspartyl-L-isoleucyl-L-Isoleucyl-L-tryptophan (SEQ ID NO: 22)

1.0 g (0.32 mmole) Fmoc-Trp-AminoTech PA500 resin is preswelled in DMF and packed into a standard MilliGen 9050 reaction column. Two residues of Fmoc-L-lle-OPfp (.665 g, 1.28 mmole) and Fmoc-L-Asp(O-t-Bu)-OPfp (0.739 g, 1.28 mmole) are coupled in sequence using the standard MilliGen protocols except that the coupling times for the lle-lle and Asp-lle couplings are extended to 120 and 90 minutes respectively. On-line acetylation with 0.5M acetic anhydride/0.5M pyridine in DMF is followed by DMF and DCM washes. The protected peptide resin is vacuum dried and cleaved with two 10 mL portions of TFA/water (90:10) +50 mg L-tryptophan as a scavenger (45 min. per portion). The crude peptide is isolated by precipitation into diethyl ether (250 mL), and purified by preparative HPLC on a Vydac C-18 (10µ) column using a gradient of acetonitrile/0.1% TFA (10–80% acetonitrile over 2 hr). Lyophilization yields the title compound.

FAB MS: (M+H)$^+$=588 AAA: Asx 1.00(1); lle 2.27(2); Trp 1.36(1) HPLC: 97.4% (Area %).

PROCEDURE B

Protected peptides are synthesized on an ABI Model 430 synthesizer, using t-Boc-based chemistry, PAM resins, and standard preformed symmetrical anhydride protocols as specified by the instrument manufacturer. Double couplings are used for the second lle in lle-lle sequences. The following side-chain protection is used: Asp(OBzl), Glu(OBzl), Cys(4-Me-Bzl), His(Tos), Tyr(2,5 di-Cl-Bzl). Tryptophan is used as its N-formyl derivative. After removal of the N-terminal t-Boc group, the resin-peptide is acetylated with acetylimidazole to give the corresponding N-acetyl peptide. The dried resin is cleaved with anhydrous HF/anisole at 0° for 1 hr. After removal of the HF, the scavengers are removed by extraction of the resin with diethyl ether. The released peptide is dissolved in acetic acid and isolated by lyophilization. When required, purification is done by preparative HPLC on a Vydac C-18 (10 µ) column using a gradient of acetonitrile/0.1% TFA (10–80% acetonitdle over 2 hr).

EXAMPLE 5

N-Acetyl-L-isoleucyl-L-isoleucyl-L-tryptophyl-L-α-aspertyl-L-valyl-L-asparagine (SEQ ID NO: 23)

According to Procedure B, t-Boc-L-Asparagine-Pam resin 0.76 g (0.5 mmole) is converted to the protected heptapeptide by standard ABI protocols, using 2 mmole of each t-Boo amino acid derivative per coupling. The second lle residue is double coupled. Acetylation is carried out on the ABI instrument using acetylimidazole in DMF. The dried resin peptide is cleaved under standard HF/anisole conditions and extracted into glacial acetic acid. After lyophilization to remove acetic acid, the N-formyl is cleaved from the Trp residue by treatment with aqueous hydroxylamine at pH 9.5 for 18 hr. The mixture is acidified to pH 4 with acetic acid, and lyophilized to give the crude peptide. Purification by preparative HPLC, and lyophilization give the title compound.

EXAMPLE 6

In a manner similar to Example 5, the following compounds may be prepared:
a) N-Acetyl-L-isoleucyl-L-isoleucyl-L-tryptophyl-L-α-aspartyl-L-valyl-β-alanine (SEQ ID NO: 24).
b) N-Acetyl-L-isoleucyl-L-isoleucyl-L-tryptophyl-L-cysteinyl-L-valyl-L-asparagine (SEQ ID NO: 25).
c) N-Acetyl-L-isoleucyl-L-isoleucyl-L-tryptophyl-L-cysteinyl-L-valyl-β-alanine (SEQ ID NO: 26).
d) N-Acetyl-L-isoleucyl-L-isoleucyl-L-tryptophyl-L-α-glutamyl-L-valyl-L-β-alanine (SEQ ID NO: 27).
e) N-Acetyl-L-isoleucyl-L-isoleucyl-L-tryptophyl-L-α-glutamyl-L-valyl-L-asparagine (SEQ ID NO: 28).

EXAMPLE 7

L-Isoleucyl-L-isoleucyl-L-tryptophyl-L-cysteinyl-L-vayl-L-asparagine (SEQ ID NO: 29)

In a manner similar to Example 5, without acetylation the title compound may be prepared.

EXAMPLE 8

In a manner similar to Example 5, using MBHA resin and double coupling of the first amino acid residue to the resin, the following compounds may be prepared:
a) N-Acetyl-L-isoleucyl-L-isoleucyl-L-tryptophyl-L-α-aspartamide (SEQ ID NO: 7).
b) N-Acetyl-L-isoleucyl-L-isoleucyl-L-tryptophyl-L-cysteinamide (SEQ ID NO: 30).
c) N-Acetyl-L-isoleucyl-L-isoleucyl-L-tryptophyl-L-α-glutamine (SEQ ID NO: 8).

EXAMPLE 9

L-Isoleucyl-L-Isoleucyl-L-tryptophyl-L-cysteinylamide (SEQ ID NO: 31)

In a manner similar to Example 8, without acetylation the title compound may be prepared.

PROCEDURE C

Protected peptides am synthesized on an ABI Model 430 synthesizer, using t-Boc-based chemistry on an oxime resin. Standard preformed symmetrical anhyddde protocols are used as specified by the instrument manufacturer, except that removal of the t-Boc protecting groups is accomplished by the use of 25% TFA in DMF to protect the peptide-resin linkage. The first amino acid derivative is double coupled to the resin, and unreacted sites on the resin are capped by acetylation with acetylimidazole. Double couplings are used for the second Ile in Ile-Ile sequences. The following side-chain protection is used: Asp(OBzl), Glu(OBzl). After removal of the N-terminal t-Boc group, the resin-peptide is acetylated with acetylimidazole to give the corresponding N-acetyl peptide. The dried resin is cleaved by treatment with isopropylamine in DMF to yield the protected isopropyl amide. Hydrogenation over 5% Pd/C results in the peptide amide, which is then purified by preparative HPLC, and isolated by lyophilization.

EXAMPLE 10

In a manner similar to Procedure C, the following compounds may be prepared:
a) N-Acetyl-L-isoleucyl-L-isoleucyl-L-tryptophyl-$N_1$-(2-methylethyl)-L-α-glutamine (SEQ ID NO: 10).
b) N-Acetyl-L-isoleucyl-L-isoleucyl-L-tryptophyl-$N_1$-(2-methylethyl)-L-aspartamide (SEQ ID NO: 12).

PROCEDURE D

The hydroxamic acids are prepared from the corresponding peptide carboxylic acids by addition of HOSu and EDC to a solution of the peptide in DMF at 0°. The active ester mixture is warmed to room temperature; a suspension of hydroxylamine hydrochloride and triethylamine in DMF is added, and the mixture stirred overnight. The reaction mixture is concentrated, extracted into ethyl acetate, washed with dilute HCl, saturated sodium bicarbonate, and saturated sodium chloride. Concentration of the dried organic extract yields the peptide hydroxamic acid, which is purified by preparative HPLC.

EXAMPLE 11

In a manner similar to Prodecure D, the following peptide hydroxamic acids may be prepared from the corresponding peptides prepared by the method of Example 8:
a) N-Acetyl-L-isoleucyl-L-isoleucyl-L-tryptophyl-$N_5$-hydroxy-L-glutaminyl-L-valyl-L-asparaginylamide (SEQ ID NO:32)
b) N-Acetyl-L-isoleucyl-L-isoleucyl-L-tryptophyl-N-hydroxy-L-asparaginyl-L-valyl-L-aspaginylamide (SEQ ID NO: 33).
c) N-Acetyl-L-isoleucyl-L-isoleucyl-L-tryptophyl-$N_5$-hydroxy-L-glutaminylamide (SEQ ID NO: 8).
d) N-Acetyl-L-isoleucyl-L-isoleucyl-L-tryptophyl-$N_4$-hydroxy-L-aspartamide-L-asparaginylamide (SEQ ID NO: 9).

EXAMPLE 12

N-Acetyl-l-isoleucyl-L-isoleucyl-N-hydroxy-L-tryptophanamide

In a manner similar to Procedure D, the title compound is prepared from Ac-Ile-Ile-Trp synthesized by the method of Example 6.

EXAMPLE 13

L-Isoleucyl-L-Isoleucyl-N-hydroxy-tryptophanamide

In a manner similar to Procedure C, Cbz-Ile-Ile-Trp-NHOH is catalytically hydrogenated over 5% Pd/C to give the title compound.

EXAMPLE 14

In a manner similar to Procedure D, the following hydroxamic acids may be prepared from the corresponding peptide acids prepared as per Example 10.

a) N-Acetyl-L-isoleucyl-L-isoleucyl-L-tryptophyl-$N_5$-hydroxy-$N_1$-(2-methylethyl)-L-glutaminylamide (SEQ ID NO: 11).

b) N-Acetyl-L-isoleucyl-L-isoleucyl-L-tryptophyl-$N_4$-hydroxy-$N_1$-(2-methylethyl)-L-asparaginylamide (SEQ ID NO: 13).

EXAMPLE 15

By the method described in Procedure B, without N-acetylation the protected resin-peptides may be synthesized. The peptide-resin is treated with benzoyl chloride in DMF to produce the N-benzoyl derivative. Cleavage is accomplished with HF/anisole followed by isolation/purification to produce the following:

a) N-Benzoyl-L-cysteinyl-L-valyl-L-asparagine.

b) N-Benzoyl-L-cysteinyl-L-valyl-β-alanine.

c) N-Benzoyl-L-α-glutamyl-L-valyl-β-alanine.

d) N-Benzoyl-L-α-aspartyl-L-valyl-β-alanine.

EXAMPLE 16

In a manner similar to Example 15, using MBHA resin, peptide amides may be prepared for conversion to the following hydroxamic acid derivatives by the method of Procedure D:

a) $N_2$-Benzoyl-$N_5$-hydroxy-L-glutaminyl-L-valyl-L-asparaginylamide.

b) $N_2$-Benzoyl-$N_4$-hydroxy-L-asparaginyl-L-valyl-L-asparaginylamide.

EXAMPLE 17

L-isoleucyl-L-isoleucyl-L-tryptophan

A mixture of thioanisole (1 mL) and t-Boc-Ile-Ile-Trp (0.207 g, from Bachem, Inc.)is treated with 4N HCl/dioxane (10 mL) at room temperature. After overnight stirring, the crude product is isolated by concentrating at reduced pressure. Preparative HPLC (Dynamax C-8 column, isocratic elution with 20% acetonitdle in water) gives the title compound.

FAB MS: $(M+H)^+$:431

EXAMPLE 18

[2R,S]-N-[[3-Methyl-1-oxo-2-[[(phenylmethyl)thio]methyl]-butyl]-L-asparaginylamide 3-Methyl-2[(phenylmethyl)thio]methyl butanoic acid (0.72 g, 6 mmol) and L-asparagine amide (0.5 g, 5.6 mmol) am suspended in DMF (30 mL). Diisopropylethylamine (388 mg, 6 mmol), HOBt (0.46 g, 6 mmol), and DCC (0.62 g, 6 mmol) are added. The reaction is stirred at room temperature for 6 h, filtered and the filtrate chromatographed on silica gel to afford the title compound.

NMR (CDCl$_3$): δ=0.80(d,3), 0.82(d,3), 1.60–1.80(m,1), 2.20–2.60(m,5), 3.70–3.76(m,2), 4.45(m,1), 6.90–7.40(m, 9), 8.20(br t,1).

EXAMPLE 19

N-[[2-Mercaptomethyl-3-methyl-1-oxo]butyl]-L-asparaginylamide

N-[[3-Methyl-1-oxo-2-[[(phenylmethyl)thio]methyl]butyl asparaginamide (225 mg, 1.56 mmol) is added to a suspension of sodium (179 mg, 7.8 mmol) in liquid ammonia (15 mL). The reaction is stirred for 15 min. Solid ammonium chloride is added to destroy excess sodium, the ammonia allowed to evaporate and the residue chromatographed on silica gel to afford the title compound.

NMR (DMSO-d$_6$): δ=0.79–1.74(m,6), 2.20(m,1), 2.40–2.50(m,2), 2.50–2.60(m,2), 3.30–3.60(m,1), 4.50–4.60(m,1), 6.85(br s,1), 7.05(br d,1) s,1 ), 7.40(br s,1 ), 8.20(dd,0.5), 8.30(dd, 0.5).

EXAMPLE 20

In a manner similar to Example 18 and 19, the following compounds are reacted to produce the indicated compounds.

a) 3-Methyl-2[(phenylmethyl)thio]methyl butanoic and β-alanine are reacted to provide N-[(2-mercaptomethyl-3-methyl-l-oxo)butyl-β-alanine.

b) 3-Indolyl-2-[[(phenylmethyl)thio]methyl]propanoic acid is reacted with L-valinyl-L-asparagine to provide N-[N-[3-(1-indol-3-yl)- 2-(mercaptomethyl )-1-oxopropyl]-L-valyl]-L-asparagine.

c) 3-Indolyl-2-[[(phenylmethyl)thio]methyl]propanoic acid is reacted with L-valinyl-β-alanine to provide N-[N-[3-(1-indol-3-yl)- 2-(mercaptomethyl)-1-oxopropyl]-L-valyl]-β-alanine.

EXAMPLE 21

3-Phenylpropylphosphonic acid, mono[[1-(1-methylethyl)-2-oxo-2-[[ 3-oxo-3-phenylmethoxy]propyl]aminolethyl]ester (2-Hydroxy-3-methyl-l-oxo-butyl) α-alanine benzylester (1.4 g, 5 mmol) and 3-phenylpropyl phosphonic acid (1.38 g, 7.5 mmol), DMAP (0.22 g) and DCC (1.48 g, 7.2 mmol) are reacted together in THF (30 mL) for 4 h at room temperature. The reaction is filtered and treated with sodium metaperiodate (1.0 g) in water (12 mL). The reaction is stirred at room temperature for 16 h. Ethyl acetate (200 mL) is added to the reaction and the solution washed with 10% citric acid solution, saturated sodium bicarbonate, saturated sodium chloride. Drying (Na$_2$SO$_4$), evaporation of the solvent and chromatography on silica gel affords the title compound.

NMR (CDCl$_3$): δ=0.83(d,3), 0.93(d,3), 1.60–2.00(m,4), 2.20– 2.40(m, 1 ), 2.56(br s,2), 2.66(br t,2), 3.52(br d,2), 4.50(br d, 1), 5.07(dd,1), 5.08(dd, 1), 7.10–7.60(m, 11 ).

EXAMPLE 22

3-[[[2-[[Hydroxy(3-phenylpropyl)phosphinyl]oxy]-3-methyl- 1-oxo]butyl]-amino]propanoic acid The product of Example 21 (1.8 g, 3.9 mmol) is stirred with 2N NaOH (12 mmol) for 16 h. The reaction is washed with ethyl acetate and acidified to pH =3 with 2N HCl. The aqueous layer is extracted with dichloromethane, dried (Na$_2$SO$_4$) and evaporated. LiOH (440 rag, 10.5 mmol) is added followed by water (15 mL) and acetonitrile (10 mL). The solution is lyophilized to afford the title compound.

NMR (DMSO-d$_6$): δ=0.70(d,3), 0.80(d,3), 1.40(m,2), 1.70–1.80(br m,2), 2.00–2.20(m,2), 2.40(br s,2), 2.60(t,2), 3.10(br m,1), 4.20(d,1), 7.10–7.30(m,6).

EXAMPLE 23

In a manner similar to Example 21 and 22 the following compounds are reacted to produce the indicated compounds.

a) (2-Hydroxy-3-phenyl-1-oxopropyl) β-alanine benzylester and 3-phenylpropyl phosphonic acid are reacted together to provide N-[2-[[hydroxy(3-phenylpropyl)phosphinyl]oxy]-1-oxopropyl]-β-alanine.

b) (2-Hydroxy-3-indolyl)-1-oxopropyl β-alanine benzylester and 3-phenylpropyl phosphonic acid are reacted together to provide N-[2-[[hydroxy(3-phenylpropyl)phosphinyl]oxy]-3-(1H-indol- 3-yl)-1-oxopropyl]-L-asparagine.

EXAMPLE 24

N-[N-(4-phenylbutyl)ethoxyphosphinyl-L-valyl]-βalanine methyl ester

Ethyl(4-phenylbutyl) phosphinic acid (5.2 g, 21.5 mmol) is coupled with L-valyl-β-alanine methyl ester (5.13 g, 21.5 mmol) using diphenylphosphoryl azide (4.63 mL, 21 mmol) and triethylamine (42 mmol) in acetonitrite to afford the title compound.

NMR (CDCl$_3$): δ=0.91(m,6), 1.27(m,3), 1.67(m,6), 1.98(m,1), 2.53(t,2), 2.60(m,2), 3.28(t,1), 3.51(m,3), 3.67(s, 3), 3.85–4.05(m,2), 7.17(t,3), 7.25(t,2).

EXAMPLE 25

N-[N-(4-Phenylbutylphosphinyl)-L-valyl]-β-alanine

N-[N-(4-Phenylbutyl)ethoxyphosphinyl-L-valyl]-β-alanine methyl ester (0.12 g, 0.28 mmol)is heated with 6N NaOH (3 mL) and EtOH (3 mL) for 1 h at 50° C. The mixture is then treated with crushed dry ice for 30 min. The mixture is filtered and the filtrate is washed with methanol and evaporated (procedure repeated twice) to give the title compound.

NMR (D$_2$O): δ=0.85(d,3), 0.90(d,3), 1.50(m,4), 1.65(t,2), 1.94(m,1), 2.37(t,2), 3.35(m,3), 7.31(m,5).

EXAMPLE 26

In a manner similar to Examples 24 and 25, the following compounds are reacted to produce the indicated compounds:

a) Ethyl (4-phenylbutyl) phosphinic acid is coupled with L-phenylalanyl β-alanine methyl ester and hydrolyzed to afford N-[N-( 4-phenylbutyl)phosphinyl-L-phenylalanyl]-β-alanine.

b) Ethyl (4-phenylbutyl) phosphinic acid is coupled with L-leucyl-L-tryptophan methyl ester and hydrolyzed to afford N-[N-( 4-phenylbutyl)phosphinyl-L-leucyl]-L-tryptophan.

EXAMPLE 27

N-[N-(4-Phenylbutyl)ethoxyphosphinyl-L-valyl]-β-alanlnamide

The product of Example 26a (0.3 g, 0.7 mmol) is treated with concentrated ammonium hydroxide (1 mL) and methanol (1 mL) in a sealed tube. The volatile materials are evaporated and the residue chromatographed on silica gel to afford the title compound.

NMR (CDCl$_3$): δ=0.89–0.94(m,6), 1.27(m,3), 1.66(m,6), 1.95(m,1), 2.43(t,2), 2.60(t,2), 3.40(m,1), 3.52(m,3), 4.00(m,2), 5.95(br d,1), 6.55(br d,1), 7.14(t,3), 7.27(t,2), 7.60(t,1).

EXAMPLE 28

N-[N-(4-Phenyl)butylphosphinyl-L-valyl]-β-alaninamide

The product of Example 27 is reacted as in Example 25 to afford the title compound.

NMR (D$_2$O): δ=0.82(d,3), 0.88(d,3), 1.45–1.55(m,4), 1.65(t,2), 1.92(m,1), 2.42(t,2), 2.63(t,2), 3.30(dd,1), 3.38(t, 2), 7.30(m,5).

EXAMPLE 29

N-(1-Diethoxyphosphinyl-3-phenylpropyl)-L-valine

Triethylphosphite (7.09 g, 42.7 mmol), L-valine (5 g, 42.7 mmol) and hydrocinnamaldehyde (5.73 g, 42.7 mmol) are heated in acetic acid (15 mL) at 80° C. for 4 h. After evaporating the solvent, the solid is dissolved in 5% sodium bicarbonate solution, washed with ether and acidified to pH =4. The aqueous mixture is extracted with ethyl acetate, dried and evaporated to afford the title compound.

NMR (CDCl$_3$): δ=0.92–1.00(m,6), 1.22–1.37(m,6), 1.80–2.00(m,1), 2.00–2.20(m,2), 2.60–3.00(m,3), 3.25(d, 0.5), 3.50(d, 0.5), 4.13–4.16(m,4), 7.10–7.35(m,5).

EXAMPLE 30

[N-(1-Diethoxyphosphinyl-3-phenylpropyl)-L-valine]-β-alenine methyl ester

The product of Example 29 (660 rag, 1.86 mmol) and β-alanine methyl ester hydrochloride (260 rag, 1.86 mmol) are coupled in THF (5 mL) using methods described in Example 18 to afford the title compound as mixture of diastereomers.

NMR (CDCl$_3$): δ=0.80–1.00(m,6), 1.20–1.40(m,6), 1.80–2.20(m,3), 2.45(dd, 1.33), 2.50(dd, 0.67), 2.60–2.80(m,2), 2.80–3.00(m,1), 3.10(d,0.33), 3.30(d, 0.67), 3.40–3.60(m,2), 3.62(s,1), 4.00–4.20(m,4), 7.10–7.30(m,6.5), 7.80(br t,0.5).

EXAMPLE 31

N-[N-(3-Phenyl-1-dihydroxyphosphinyl propyl)-L-valyl]-β-alanine

The product of Example 30 (192 mg, 0.42 mmol) is treated with trimethylsilyl bromide (0.5 mL, 3.8 retool) for 18 h. After evaporating the volatiles, methanol (3 mL) is added and the reaction is stirred for 2 h. 2N NaOH (30 mL) is added followed by methanol (15 mL). After stirring for 1 h, the reaction is evaporated, redissolved in water (20 mL) and acidified to pH =7 with 1N HCl. Evaporation of water and ion exchange chromatography on DOWEX-50 H$^+$, affords the title compound.

NMR (DMSO-d$_6$, TFA added): δ=0.90–1.02(m,6), 2.0–2.20(m,3), 2.4– 2.9(m,5), 3.1–3.5(m,2), 4.0(d, 0.5), 4.2(d, 0.5), 7.2–7.3(m,5), 8.7(m,0.5), 8.92(br t,0.5), 9.0(d, 0.5).

EXAMPLE 32

(±)-[1-(Hydroxyphenoxyphosphinyl)-2-phenylethyl]carbamic acid phenylmethyl ester

[1-(Diphenoxyphosphinyl)-2-phenylethyl]carbamic acid phenylmethyl ester (prepared by the method of J. Oleksyszyn et al. Synthesis 985 (1979)) (1.46 g, 3.0 mmol) is suspended in acetonitrile (10 mL) and 1.5 N LiOH (6.5 mL) is added. The mixture is stirred at room temperature for h, after which it is diluted with water, saturated with $NaHCO_3$, and extracted with methylene chloride. The aqueous layer is acidified to pH 1 with 2N HCl, extracted with methylene chloride, and the organic extracts are dried over sodium sulfate and evaporated. The residue is recrystallized from acetonitrile to give the title compound.

NMR ($CDCl_3$): δ=2.80(m,1), 3.20(m,1), 4.51(m,1), 4.97(m,2), 5.25(d,1 ), 7.09–7.27(m,15).

EXAMPLE 33

[1-(Hydroxymethoxyphosphinyl)-2-(1H-indol-3-yl)ethyl]carbamic acid phenylmethyl ester

[1-(Dimethoxyphosphinyl)-2-(1H-indol-3-yl)ethyl]carbamic acid phenylmethyl ester (prepared by the method of M. Tishler et al. Tetrahedron Lett. 5461 (1983)) (4.98 g, 12.4 retool) is dissolved in methanol (80 mL) and 2N NaOH (20 mL) and the mixture is allowed to stand at room temperature for 3 days. The mixture is diluted with water, washed twice with methylene chloride, acidified with 2N HCl, and extracted three times with methylene chloride. The organic extracts are dried over sodium sulfate and evaporated to a residue, which is recrystallized from acetonitdle to give the title compound.

NMR (DMSO-$d_6$): δ=2.90(m,1), 3.14(m,1), 3.61(d,3), 4.03(m,1), 4.92(s,2), 6.93–7.36(m,8), 7.53(d,1), 7.62(d,1), 10.84(br s,1).

EXAMPLE 34

(±)-[1-(Hydroxymethoxyphosphinyl)-2-phenylethyl]carbamic acid phenylmethyl ester In a manner similar to that described in Example 33, [1-(dimethoxyphosphinyl)- 2-phenylethyl]carbamic acid phenylmethyl ester is conveyed to the title compound.

EXAMPLE 35

N-[N-[[2-(1H-indol-3-yl)-1[[(phenylmethoxy)carbonyl]amino]-ethyl]methoxyphosphinyl]-L-valyl]-β-alanine ethyl ester Using the method of K. Yamauchi et al. J Org. Chem. 49, 1158 (1984) the product of Example 33, (5.01 g, 12.9 mmol), N-(L-valyl)-β-alanine ethyl ester hydrochloride (3.91 g, 15.5 mmol), diphenylphosphoryl azide (4.27 g, 15.5 mmol), and triethylamine (3.14 g, 31.0 mmol) are combined in acetonitrile (125 mL) under an argon atmosphere and stirred at room temperature for 10 days. The mixture is then diluted with methylene chloride, washed with water, 0.5N NaOH, and brine, and dried over sodium sulfate. The solvent is evaporated and the residue is chromatographed on silica gel to afford the title compound.

NMR ($CDCl_3$): δ=0.60–0.97(m,6), 1.22(m,3), 1.93(m,1), 2.51(m,2), 2.81–3.81(m,9), 4.11(m,2), 4.41(m,1), 5.00(m,2), 5.20–5.81(m,1), 6.79(m,1), 7.06–7.42(m, 1 ), 7.63(m, 1 ), 8.11 (m, 1 ).

EXAMPLE 36

In a manner similar to that described in Example 35, the following reactants:

a) The product of Example 34 and N-(L-valyl)-β-alanine ethyl ester hydrochloride;

b) The product of Example 34 and L-valine amide hydrochloride;

are converted respectively to:

c) N-[N-[[[2-Phenyl-1-[[(phenylmethoxy)carbonyl]amino]ethyl]-methoxyphosphinyl] -L-valyl-β-alanine ethyl ester and d) [1-[[[1-(Aminocarbonyl)-2-methylpropyl]amino]methoxy-phosphinyl]- 2-phenylethyl]carbamic acid phenylmethyl ester

EXAMPLE 37

N-[N-I[2-(1H-Indol-3-yl)-1-[[(phenylmethoxy)carbonyl]amino]-ethyl]hydroxyphosphinyl]-L-valyl-β-alanine The product of Example 35 (203 rag, 0.35 mmol) is suspended in dioxane (2 mL) and 1.5N LiOH (2 mL) is added. The mixture is stirred at room temperature for 18 h, after which the solvent is evaporated, the residue is suspended in ethanol, and the solvent is evaporated again. The residue s dissolved in water, and the mixture is filtered and lyophillized to give the title compound.

NMR ($D_2O$): δ=0.85–0.92(m,6), 1.93(m,1), 2.33(m,2), 2.87(m,1), 3.14–3.59(m,3), 3.86(m,1), 4.23(m,1), 6.57(m,1), 7.03(m,1), 7.17(m,4), 7.35(m,2), 7.51 (d,1), 7.72(d,1 ).

EXAMPLE 38

In a manner similar to that described in Example 37, the following reactants:

a) The product of Example 36c;

b) N-[[2-Phenyl-1-[[(phenylmethoxy)carbonyl]amino]ethyl]methoxyphosphinyl]-L-valine amide;

c) The product of Example 36d are converted to the following products respectively:

d) N-[N-[[2-Phenyl-1-[[(phenylmethoxy)carbonyl]amino]ethyl]hydroxyphosphinyl]-L-valyl]-β-alanine;

e) [1-[[[1-(Aminocarbonyl)-2-methylpropyl]amino]hydroxy-phosphinyl]- 2-(1H-indol-3-yl)ethyl]carbamic acid phenylmethyl ester; and f) [1-[[[1-(Aminocarbonyl)-2-methylpropyl]amino]hydroxyphosphinyl]- 2-phenylethyl]carbamic acid phenylmethyl ester.

EXAMPLE 39

N-[N-[[2-(1H-Indol-3-yl)-1-[[(phenylmethoxy)carbonyl]amino]ethyl]hydroxyphosphinyl]-L-valyl]-β-alaninylamide The product of Example 35 (201 mg, 0.34 mmol) is suspended in a mixture of dioxane (5 mL) and concentrated ammonium hydroxide (5 mL) and the mixture is stirred for 15 days. 1.5N LiOH (0.46 mL) is added, and the mixture is evaporated. The residue is chromatographed on silica gel and recrystallized from methanol/ethyl ether to give the title compound.

NMR (D$_2$O): δ=0.86–0.93(m,8), 1.91(m,1), 2.40(m,2), 2.81(m,1), 3.20–3.55(m,4), 3.85(m,1), 4.20(d,1), 4.51–4.90(m,2), 6.54(br s,1) 7.04–7.36(m,7), 7.47(d,1), 7.70(d,1).

EXAMPLE 40

N-[N-[[2-Phenyl-1-[[(phenylmethoxy)carbonyl]amino]ethyl]hydroxyphosphinyl]-L-valyl]-β-alaninylamide In a manner similar to that described in Example 39, the product of Example 36c is converted to the title compound.

EXAMPLE 41

N-[N-(Carboxymethyl)-L-valyl]-β-alanine

To a 0° C. solution of 1.8 g of N-(2-methoxy-2-oxoethyl)-L-valine (prepared by the method descd by T. Miyazawa, Bull. Chem. Soc. Jpn. 5:3, 555, (1980)), 3.4 g of β-alanine benzyl ester p-toluenesulfonate salt, 2.7 mL of triethylamine, and 1.3 g of HOBt in 100 mL of DMF is added 1.9 g of EDC. The reaction mixture is warmed to room temperature and stirred for 18 h. The DMF is removed by distillation in vacuo (50° C., 1 mm) and the residue is chromatographed on silica gel eluting with a mixture of dichloromethane:methanol, 98:2, to afford N-[N-(2-methoxy-2-oxoethyl)-L-valyl]alanine benzyl ester.

To a 5° C. solution of 0.57 g of N-[N-(2-methoxy-2-oxoethyl)-L-valyl]-β-benzyl ester in 30 mL of 2:1, THF:H$_2$O is added 0.22 g of lithium hydroxide. The solution is warmed to room temperature, stirred for 4 h, brought to a pH=4 with 1N HCl, and evaporated. The residue is slowly added to a strong acid ion exchange resin and eluted with 2–4% pyddine in water. The ninhydrin active fractions are combined and lyophilized to afford the title compound.

$^1$H NMR (DMSO-d$_6$): δ=0.86(d,6), 1.81(m,1), 2.39(t,2), 2.82(d,1), 3.03(d, 1), 3.18(d, 1), 3.28(m,3), 8.06(br t, 1).

EXAMPLE 42

N-[N-(Carboxymethyl)-L-valyl]-β-alaninamide

To a 5° C. solution of 1.48 g of N-(2-methoxy-2-oxoethyl)-L-valine (prepared as described above), 1.26 g of β-alanine amide, and 2.4 mL of triethylamine in 60 mL of DMF was added 1.83 mL of diphenylphosphoryl azide. The reaction mixture was warmed to room temperature and stirred for 18 h. The DMF is removed by distillation in vacuo (50° C., 1 mm) and the residue is chromatographed on silica gel eluting with a mixture of ethyl acetate:methanol :H$_2$O, 14:2:1, to afford N-[N-(2-methoxy-2-oxoethyl)-L-valyl]-β-alanine amide.

To a 5° C. solution of 0.60 g of N-[N-(2-methoxy-2-oxoethyl)-L-valyl]-β-alanine amide in 75 mL of 2:1, THF:H$_2$O, is added 0.20 g of lithium hydroxide. The solution is warmed to room temperature, stirred for 2 h, brought to a pH=7 with 1N HCl, and evaporated. The residue is slowly added to a strong acid ion exchange resin and eluted with 5% pyridine in water. The ninhydrin active fractions are combined and lyophilized to afford the title compound.

$^1$H NMR (DMSO-d$_6$): δ=0.87(d,6), 1.82(m,1), 2.24(t,2), 2.88(d,1), 3.03(d, 1), 3.24(d, 1), 3.27(m,3), 6.82(br s, 1), 7.33(br s, 1), 8.02(br t, 1).

EXAMPLE 43

N-[N-(2-Methoxy-2-oxoethyl)-L-valyl]-L-asparaginylamide

To a 5° C. solution of 1.50 g of N-(2-methoxy-2-oxoethyl)-L-valine (prepared as described above), 1.46 g of L-asparaginamide hydrochloride, 1.34 g of HOBt, and 2.4 mL of triethylamine in 125 mL of DMF was added 1.79 g of DCC. The reaction mixture is warmed to room temperature and stirred for 18 h. The reaction mixture is filtered, the filtrate is evaporated by distillation in vacuo (50° C., 1 mm) and the residue is chromatographed on silica gel eluting with a mixture of ethyl acetate:methanol:H$_2$O, 14:2:1 to afford N-[N-(2-methoxy-2-oxoethyl)-L-valyl]-L-asparaginamide.

$^1$H NMR (DMSO-d$_6$): δ=0.87(m,6), 1.92(m,1), 2.45(d,2), 2.79(d,1), 3.31(m,2), 3.61(s,3), 4.50(quar, 1), 6.85(br s,1), 7.02(br s,1), 7.17(br s,1), 7.29(br s, 1), 8.02(d t, 1).

EXAMPLE 44

N-[N-(Carboxymethyl)-L-valyl]-L -asparaginamide

To a 0° C. solution of 0.605 g of the product of Example 43 in 45 mL of 1, THF:H$_2$O is added 0.109 g of lithium hydroxide. The solution is stirred for 2 h at 0° C., brought to a pH=7 with 1N HCl, and evaporated. The residue is slowly added to a strong acid ion exchange resin and eluted with 5% pyridine in water. The ninhydrin active fractions are combined and lyophilized to afford the title compound.

$^1$H NMR (DMSO-d$_6$): δ=0.87(d,6), 1.92(m,1), 2.46(m,2), 2.88(d,1), 3.13(d, 1), 3.27(d, 1), 4.50(quar, 1), 6.85(br s, 1), 7.03(br s, 1), 7.20(br s, 1), 7.30(br s, 1), 8.11 (dt, 1).

EXAMPLE 45

N-[N-(Carboxymethyl)-L-valyl]-L-asparagine

To a room temperature solution of 2.26 g of N-(2-methoxy- 2-oxoethyl)-L-valine (prepared as described above), 0.74 mL of triethylamine, and 0.61 g of N-hydroxysuccinimide in 25 mL of THF was added 1.09 g of DCC and the reaction mixture stirred for 18 h. The reaction mixture is filtered, the filtrate concentrated, and the residue recrystallized from a mixture of 2-propanol/ether to afford N-(2-methoxy-2-oxoethyl)-L-valine N-hydroxysuccinimide ester.

To a mixture of 1.00 g of N-(2-methoxy-2-oxoethyl)-L-valine N-hydroxysuccinimide ester in 35 mL of dimethoxymethane is added a mixture of 0.69 g of L-asparagine, and 0.44 g of sodium bicarbonate in 35 mL of water. The reaction mixture is stirred at room temperature for 18 h, the solvents evaporated on a rotoevaporator, and the residue is chromatographed on silica gel eluting with a mixture of ethyl acetate:methanol:H$_2$O, 7:2:1, to afford N-[N-(2-methoxy-2-oxoethyl)-L-valyl]asparagine.

To a 5° C. solution of 0.38 g of N-[N-(2-methoxy-2-oxoethyl)-L-valyl]asparagine in 50 mL of 1:1, THF:H$_2$O is added 0.17 g of lithium hydroxide. The solution is stirred for 2 h at 5° C., brought to a pH=7 with 1N HCl, and evaporated. The residue is slowly added to a strong acid ion exchange resin and eluted with 5% pyridine in water. The ninhydrin active fractions are combined and lyophilized to afford the title compound.

$^1$H NMR (DMSO-d$_6$): δ=0.88(t,6), 1.83(m,1), 2.55(d,2), 2.91(d,1), 3.08(d, 1 ), 3.29(d, 1 ), 4.52(quar, 1 ), 6.90(s, 1 ), 7.38(s, 1 ), 8.18(d,1).

EXAMPLE 46

N-[N-(1-Ethoxycarbonyl-3-phenylpropyl)-L-valyl]-β-alanine ethyl ester 9.8 g of hydrocinnimaldehyde is added to a solution of 25 g of L-valine benzyl ester p-toluene sulfonate salt and 3.9 g of sodium cyanide in 180 mL of methanol. The mixture is stirred at room temperature for 18 h, concentrated to near dryness, partitioned between 150 mL of water and 150 mL of dichloromethane. The aqueous is extracted with 150 mL of dichloromethane, and the combined organic extract is added (sodium sulfate), and the solvent removed with a rotoryevaporator. The residue is chromatographed on silica gel eluting with a mixture of ether:hexane, 1:1, to afford N-(1-cyano-3-phenylpropyl)-L-valine benzyl ester.

A 0° C. solution of 5.1 g of N-(1-cyano-3-phenylpropyl)-L-valine benzyl ester in 100 mL of ethanol is saturated with dry HCl gas, stored for 5 days at 0–5° C., and evaporated to a residue which is dissolved in 50 mL of acetonitrile:water, 2:1. The solution is neutralized with sodium bicarbonate, and extracted twice with 150 mL portions of dichloromethane. The combined organic extract is dried (sodium sulfate), and the solvent removed with a rotoryevaporator. The residue is chromatographed on silica gel eluting with a mixture of ether:hexane, 6:4, to afford N-(1-ethoxycarbonyl-3-phenylpropyl)-L-valine benzyl ester.

2.4 g of N-(2-ethoxycarbonyl-3-phenylpropyl)-L-valine benzyl ester is dissolved in 50 mL of ethanol, to which is added 500 mg of 10% Pd-C, and the mixture is hydrogenated at 50 psi for 3 h. The resulting mixture is filtered and the solvent removed with a rotoevaporator to afford N-(2-ethoxycarbonyl- 3-phenylpropyl)-L-valine.

To a 0° C. solution of 1.8 g of N-(2-ethoxycarbonyl-3-phenylpropyl)-L-valine, 1.1 g of β-alanine ethyl ester hydrochloride, 2.3 mL of triethylamine, and 1.0 g of HOBt in 100 mL of DMF is added 1.4 g of EDC. The reaction mixture is warmed to room temperature and stirred for 18 h. The DMF is removed by distillation in vacuo (50° C., 1 mm) and the residue is chromatographed on silica gel eluting with a mixture of dichloromethane:methanol, 98:2 to afford the title compound.

$^1$H NMR (DMSO-d$_6$): δ=0.86(dd,6), 1.18(m,6), 1.66(m, 1), 1.82(quar,2), 2.22–2.30(br re,1), 2.44(t,2), 2.48–2.78(m, 3), 3.03(m,1), 3.18–3.40(m,2), 3.98–4.12(m,4), 7.12–7.33(m,5), 8.02(t,1).

EXAMPLE 47

N-[N-(1-Carboxy-3-phenylpropyl)-L-valyl]-1-β-alanine

To a 5° C. solution of 0.80 g of the product of Example 46 in 125 mL of 1:1, THF:H$_2$O is added 0.33 g of lithium hydroxide. The solution is stirred for 2 h at 5° C., brought to a pH=7 with 1N HCl, and evaporated. The residue is slowly added to a strong acid ion exchange resin and eluted with 5% pyridine in water. The ninhydrin active fractions are combined and lyophilized to afford the title compound.

$^1$H NMR (DMSO-d$_6$): δ=0.83–0.92(m,6), 1.72(m,1), 1.81(m,2), 2.38(t,2), 2.65–2.80(m,2), 2.95(t, 0.2), 3.02(t, 0.8), 3.03(m,1), 3.15–3.45(m,3), 7.16–7.31(m,2), 7.86(t, 0.2), 8.02(t, 0.8).

EXAMPLE 48

(±)-3-Methyl-2-[[(phenylmethoxy)amino]carbonyl]butanoic acid

KOH (0.519 g) dissolved in ethanol (4 mL) and water (2 mL) is added to a stirred solution of ethyl 2-[(phenylmethoxyamino)carbonyl]-3-methylbutanoate (1.0 g) dissolved in ethanol (4 mL). After 2 days, the ethanol is evaporated, and water (10 mL) is added. The mixture is filtered, and the filtrate acidified with HCl. The product is collected by filtration to provide the title compound.

NMR (CDCl$_3$): δ=0.93(3H,d) 0.95(3H,d), 2.24 (1 H,m), 2.81(1H,d), 4.89(2H,s), 7.34(5H,m).

EXAMPLE 49

N-[2-[(Hydroxyamino)carbonyl]-3-methyl-1-oxobutyl]-β-alanine.

The product of Example 48 is coupled with β-alanine t-butyl ester hydrochloride utilizing DCC, HOBt and ethyldiisopmpylamine in the usual manner. Hydrolysis of the t-butyl ester and benzyl groups is accomplished with methanol and 5% Pd-C. Removal of the catalyst, evaporation of the solvent and purification by HPLC (C-18) provides the title compound.

NMR (MeOH): δ=0.946(6H,d), 2.22(1H,m), 2.49(2H,t), 2.54(1H,d), 3.42(2H,m).

EXAMPLE 50

N$_2$-[2-[(Hydroxyamino)carbonyl]-3-methyl-1-oxobutyl]-L-asparagine

N-[2-[(Phenylmethoxyamino)carbonyl]-3-methylbutanoyl]-L-asparagine 1,1-dimethylethyl ester (100 rag)is dissolved in trifluoroacetic acid. After 1 h, the solvent is evaporated, and the residue is triturated with ether. The resultant solid is dissolved in methanol and hydrogenated over 5% Pd-C. Removal of the catalyst, evaporation of the solvent, and purification by HPLC (C-18) provides the title compound.

NMR (MeOH): δ=1.00(6H,m), 2.30(1H,m), 2.60 (1 H,d), 2.78(2H,m), 4.70(1H,m).

EXAMPLE 51

2-(1-Methylethylidene)butanedioic acid 4-phenylmethyl ester

Dihydro-3-(methylethylidine)-2,5-furandione, benzyl alcohol (14.36 g, 133 mmol), and ethanol-free chloroform (110 mL) are refluxed for three days. Evaporation of the solvent followed by recrystallization from ethyl acetate and hexanes provides the title compound.

NMR (CDCl$_3$); δ=1.90(3H,s), 2.23(3H,s), 3.46(2H,s), 5.14(2H,s), 7.34 (5H, m).

EXAMPLE 52

(±)-N-[[4-(Hydroxyamino)-2-(1-methylethyl)-1,4-dioxo]butyl]-β-alanine

N-[[2-(1-Methylethyl)-4-[(phenylmethoxy)amino]-1,4-dioxo]butyl]-β-alanine, (127 mg)in methanol (1.5 mL) is hydrogenated over 5% Pd-C for 10.5 h to provide crude product. Purification is accomplished with HPLC on a C-18 column (MeCN, water, TFA).

NMR (MeOH): δ=0.92(3H,d), 0.94(3H,d), 1.80(1H,m), 2.28(2H,m), .46(3H,m), 3.40(2H,m).

EXAMPLE 53

$N_2$-[2-(1-Methylethyl)-1,4-dioxo-4-[(phenylmethoxy)amino] butyl]-L-asparagine, tert-butyl ester N-[2-(1-Methylethylidine )-1,4-dioxo-4-hydroxybutyl]-L-asparagine 1,1-dimethylethyl ester, and benzyloxyamine are coupled with DCC in the usual manner. Chromatography on silica gel (chloroform methanol) provides the title compound.

NMR (CDCl$_3$): δ0.94(3H,m), 0.96(3H,m), 1.42(4.5H, s), 1.46(4.5H,s), 1.84(1H,m), 2.28(1H,m), 2.45(1H,m), 4.30(0.5H,m), 4.76(0.5H,m), 4.86 (2H,m), 6.19 (0.5H, s), 6.38 (0.5H, s), 6.46(0.5H,s), 6.59(0.5H, s), 7.35(5H,m), 8.19(0.5H, d), 9.68(1H,d).

EXAMPLE 54

$N_2$-[2-(1-Methylethyl)-1,4-dioxo-4-butyl]-L-asparagine

The product of Example 53 (470 mg)is hydrolyzed with TFA (4.5 mL) at 0° C. for 1 h and 20° C. for 1 h. The TFA is evaporated and the residue is 10 triturated with ether and then lyophilized from water to provide the title compound.

NMR (MeOH): δ=0.93(6H,m), 1.82(1H,m), 2.28(1H,dd), 2.36(1H,dd), 2.55(1H,m), 2.74(2H,m), 4.80(3H,m), 7.35(5H,m), 8.18(1H,t).

EXAMPLE 55

$N_2$-[4-(Hydroxyamino)-2-(1-methylethyl)-1,4-dioxobutyl]-L- asparagine

The product of Example 54 (114 mg)in methanol (3 mL)is hydrogenated over 5% Pd-C for 1.25 h to provide the title compound.

NMR (MeOH): δ=0.96(6H,m), 1.84(1H,m), 2.32(2H,m), 2.55(1H,m), 2.74(2H,m), 4.66(0.5H,t), 4.79(0.5H, t).

---

We claim:

1. A method for the inhibition of the conversion of big endothelin to endothelin in a subject comprising administering to said subject in need of said inhibition an effective amount of a compound selected from the group consisting of the following Formulae I–VI:

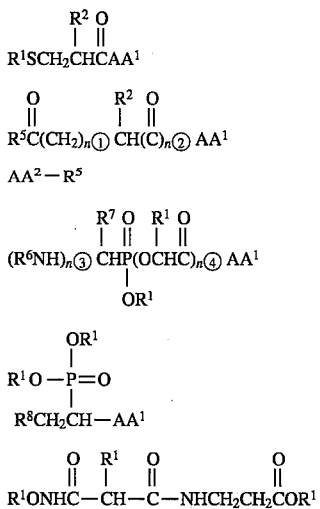

$R^1SCH_2CHCAA^1$     I $R^5C(CH_2)_{n①}CH(C)_{n②}AA^1$     II $AA^2-R^5$     III $(R^6NH)_{n③}CHP(OCHC)_{n④}AA^1$     IV
with $R^7$, $R^1$ groups and $OR^1$ $R^1O-P(=O)(OR^1)-R^8CH_2CH-AA^1$     V $R^1ONHC(=O)-CH(R^1)-C(=O)-NHCH_2CH_2COR^1$     VI wherein $R^1$ is H, alkyl, cycloalkyl, cycloalkylalkyl, phenyl, aralkyl;

$R^2$ is H, alkyl, phenyl, aralkyl, (3-indolyl)methylene, $NHR^3$;

$AA^1$, is $OR^1$ $NH_2$, val-$OR^1$, val-$NH_2$, val-Asn-$OR^1$, val-Asn-$NH_2$, val-β-Ala-$NH_2$, val-β-Ala-$OR^1$, val-Asn-Thr-$OR^1$, val-Asn-Thr-Pro-$OR^1$(SEQ ID NO:1), val-Asn-Thr-Pro-Glu-$NH_2$ (SEQ ID NO:2), Asn-$OR^1$, Asn-$NH_2$, Asn-Thr-$OR^1$, Asn-Thr-Pro-$OR^1$, Asn-Thr-Pro-Glu-$NH_2$ (SEQ ID NO: 3), β-Ala-$OR^1$, β-Ala-$NHR^1$, TrP-$OR^1$, Trp-$NH_2$, Trp-β-Ala-$OR^1$, Trp-NH-$R^1$;

$R^3$ is H, acetyl, benzoyl, $AA^2$;

$AA^2$ is $R^4$-Trp, $R^4$-Ile-Trp, $R^4$-Ile-Ile-TrP, $R^4$-Asp-Ile-Ile-Trp (SEQ ID NO:4), $R^4$-($OR^1$)Asp-Ile-Ile-Trp (SEQ ID NO:5), with the proviso that in formula III $AA^2$ must be at least three amino acids in length;

$R^4$ is H, acetyl, benzoyl, carbobenzyloxy, t-butoxycarbonyl;

$R^5$ is $OR^1$, $NHOR^1$;

$n^①$ is 0, 1, 2;

$n^②$ is 0, 1 and when in Formula II $R^2=NHR^3$, $n^②$ cannot be zero;

$n^③=0$, 1 and when absent it is replaced by H;

$n^④$ 0, 1;

$R^6$ is $R^4$, $AA^2$, $R^4$-Ile, $R^4$-Ile-Ile, $R^4$-Asp-Ile-Ile $R^4-(OR^1)$Asp-Ile-Ile;

$R^7$ is $R^1$, (3-indolyl)methylene;

$R^8$ is $R^7$, $NHR^6$, or a pharmaceutically acceptable salt thereof.

2. A method of claim 1 which comprises administering a compound of formula I which is [2RS]-N-[[3-methyl-1-oxo-2-[[(phenylmethyl)thio]methyl]butyl]-L-asparaginylamide.

3. A method of claim 1 which comprises administering a compound of formula which is N-[[2-mercaptomethyl-1-oxo]butyl]-L-asparaginylamide.

4. A method of claim 1 which comprises administering a compound of formula I which is N-acetyl-L-α-aspartyl-L-isoleucyl-L-isoleucyl-L-tryptophyl-L-cysteinylamide (SEQ ID NO:21).

5. A method of claim 1 which comprises administering a compound of formula I which is N-acetyl-L-cysteinyl-L-valyl-L-asparagyl-L-threonyl-L-prolyl-L-α-glutamine (SEQ ID NO:16).

6. A method of claim 1 which comprises administering a compound of formula II which is N-[N-(carboxymethyl-L-valyl]-β-alanine.

7. A method of claim 1 which comprises administering a compound of formula II which is N-acetyl-L-α-aspartyl-L-valyl-L-asparagyl-L-threonyl-L-prolyl-L-α-glutamine (SEQ ID NO:14).

8. A method of claim 1 which comprises administering a compound of formula II which is N-acetyl-L-α-glutamyl-L-valyl-L-asparagyl-L-threonyl-L-prolyl-L-α-glutamine (SEQ ID NO:15).

9. A method of claim 1 which comprises administering a compound of formula II which is N-[N-(carboxymethyl-L-valyl]-β-alaninamide.

10. A method of claim 1 which comprises administering a compound of formula II which is N-[N-carboxymethyl)-L-valyl]-L-asparaginylamide.

11. A method of claim 1 which comprises administering a compound of formula II which is N-[N-(2-methoxy-2-oxoethyl)-L-valyl]-asparaginylamide.

12. A method of claim 1 which comprises administering a compound of formula II which is N-acetyl-L-α-aspartyl-L-isoleucyl-L-isoleucyl-L-tryptophyl-L-α-glutamyl-L-valyl-L-asparaginyl-L-threonyl-L-prolyl-L-α-glutamine (SEQ ID NO:17).

13. A method of claim 1 which comprises administering a compound of formula II which is N-acetyl-L-α-aspartyl-L-isoleucyl-L-isoleucyl-L-tryptophyl-L-α-aspartyl-L-valyl-L-asparaginyl-L-threonyl-L-prolyl-L-α-glutamine (SEQ ID NO:18).

14. A method of claim 1 which comprises administering a compound of formula II which is N-acetyl-L-α-aspartyl-L-isoleucyl-L-isoleucyl-L-tryptophyl-L-α-aspartamide (SEQ ID NO:19).

15. A method of claim 1 which comprises administering a compound of formula II which is $N_2$-[N-acetyl-L-α-aspartyl-L-isoleucyl-L-isoleucyl-L-tryptopyhyl]-L-α-glutamine.

16. A method of claim 1 which comprises administering a compound of formula II which is N-[N-(carboxymethyl)-L-valyl-L-asparagine.

17. A method of claim 1 which comprises administering a compound of formula II which is (±)-3-methyl-2-[[(phenylmethoxy)amino]carbonyl]butanoic acid.

18. A method of claim 1 which comprises administering a compound of formula II which is N-[2-[(hydroxyamino)-carbonyl]-3-methyl-1-oxobutyl]-L-asparagine.

19. A method of claim 1 which comprises administering a compound of formula II which is N-[N-(1-carboxy-3-phenylpropyl)-L-valyl]-β-alanine .

20. A method of claim 1 which comprises administering a compound of formula II which is N-acetyl-L-α-aspartyl-L-isoleucyl-L-isoleucyl-L-tryptophyl-L-α-glutamide (SEQ ID NO:20).

21. A method of claim 1 which comprises administering a compound of formula II which is (±)-2-(1-methylethyl)-4-oxo-4-[(phenylmethoxy)amino[butanoic acid.

22. A method of claim 1 which comprises administering a compound of formula II which is (±)-N-[[4-(hydroxyamino)-2-(1-methyethyl)- 1,4-dioxo]butyl]-β-alanine.

23. A method of claim 1 which comprises administering a compound of formula II which is N-[2-(1-methylethyl)-1, 4-dioxo- 4](phenylmethoxy)amino]butyl]-L-asparagine.

24. A method of claim 1 which comprises administering a compound of formula II which is N-[2-(1-methylethyl)-1, 4-dioxo- 4-[(phenylmethoxy)amino]butyl]-L-asparagine.

25. A method of claim 1 which comprises administering a compound of formula II which is N-[4-(hydroxyamino)-2(1-methylethyl)- 1,4-dioxobutyl]-L-asparagine.

26. A method of claim 1 which comprises administering a compound of formula III which is L-isoleucyl-L-isoleucyl-L-tryptophan.

27. A method of claim 1 which comprises administering a compound of formula III which is N-acetyl-L-α-aspartyl-L-isoleucyl-L-isoleucyl-L-tryptophan (SEQ ID NO :22).

28. A method of claim 1 which comprises administering a compound of formula IV which is 3-phenylpropyl-phosphonic acid, mono[[1-(1-methylethyl)-2-oxo-2-[[[3-oxo-3-phenylmethoxy]-propyl]amino]ethyl]ester.

29. A method of claim 1 which comprises administering a compound of formula IV which is 3-[[[2-]]hydroxy(3-phenylpropyl)phosphinyl]oxy]-3-methyl-1oxy]-butyl]amino]propanoic acid 30. A method of claim 1 which comprises administering a compound of formula IV which is (±)-1-(hydroxyphenoxy-phosphinyl)-2-phenylethyl]carbamic acid phenylmethyl ester.

31. A method of claim 1 which comprises administering a compound of formula IV which is (±)-1-(hydroxymethoxy-phosphinyl)-2-phenylethyl]carbamic acid phenylmethyl ester.

32. A method of claim 1 which comprises administering a compound of formula IV which is carbamic [1-(hydroxyphenoxy-phosphinyl)-2phenylethyl]carbamic acid phenylmethyl ester.

33. A method of claim 1 which comprises administering a compound of formula IV which is [1-[[[1-(amioncarbonyl)-2-methylpropyl]amion]hydroxyphosphinyl]-2-(1H-indol-3-yl)ethyl]carbamic acid phenylmedthyl ester.

34. A method of claim 1 which comprises administering a compound of formula IV which is [1-[[[1-(aminocarbonyl)- 2amino]methoxyphosphinyl]-2-phenylethyl]carbamic acid phenyl-methyl ester.

35. A method of claim 1 which comprises administering a compound of formula IV which is [1-[[[1-(aminocarbonyl)-2-methylpropyl)amino]hydroxyphosphinyl]-2-phenylethyl]carbamic acid phenyl-methyl ester.

36. A method of claim 1 which comprises administering a compound of formula IV which is N-[N-(4-phenylbutylphosphinyl)-L-valyl]-βalanine disodium salt.

37. A method of claim 1 which comprises administering a compound of formula IV which is N-[N-[[2-phenyl-1-[[(phenylmethoxy)carbonyl]amino]ethyl]methoxyphosphinyl]-L-valyl-β-alanine ethyl ester.

38. A method of claim 1 which comprises administering a compound of formula IV which is N-[N-[[2-(1H-indol-3-yl)- 1-[[(phenylmethoxy)carbonyl]amino]ethyl]methoxyphosphinyl]-L-valyl]-β-alanine ethyl ester.

39. A method of claim 1 which comprises administering a compound of formula IV which is N-[N-[[2-(1H-indol-3-yl)- 1-[[(phenylmethoxy)carbonyl]amino]ethyl]hydroxyphosphinyl]-L-valyl-β-alanine.

40. A method of claim 1 which comprises administering a compound of formula IV which is N-[N-[[2-phenyl- 1-[[(phenylmethoxy)carbonyl]amino]ethyl]hydroxyphosphinyl]-L-valyl]-β-alanine.

41. A method of claim 1 which comprises administering a compound of formula IV which is N-[N-(4-phenylbutyl)-ethoxyphosphinyl-L-valyl]-β-alaninamide.

42. A method of claim 1 which comprises administering a compound of formula IV which is N-[N-(4-phenylbutyl)-ethoxyphosphinyl-L-valyl]-β-alanine methyl ester.

43. A method of claim 1 which comprises administering a compound of formula IV which is N-[N-(4-phenyl)butyl-phosphinyl-L-valyl]-β-alaninamide.

44. A method of claim 1 which comprises administering a compound of formula IV which is N-[N-[[2-phenyl-1[[(phenylmethoxy)carbonyl]amino]ethyl]hydroxyphosphinyl]-L-valyl]-β-alaninamide.

45. A method of claim 1 which comprises administering a compound of formula IV which is N-[N-[[2-(1H-indol-3-yl)- 1-[[(phenylmethoxy)carbonyl]amino]ethyl]hydroxyphosphinyl]-L-valyl]-β-alaninamide.

46. A method of claim 1 which comprises administering a compound of formula V which is [N-(1-diethoxyphosphinyl-3-phenylpropyl)-L-valine]-β-alanine methyl ester.

47. A method of claim 1 which comprises administering a compound of formula V which is N-[N-3-phenyl-1-dihydroxyphosphinylpropyl)-L-valyl]-β-alanine.

48. A method of claim 1 which comprises administering a compound of formula V which is N-(1-diethoxyphosphinyl-3-phenylpropyl)-L-valine.

49. A method of claim 1 which comprises administering a compound of formula VI which is N-[2-[(hydroxyamino)carbonyl]-3-methyl-1-oxobutyl]-β-alanine.

50. A compound of the following formula I:

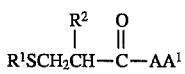

wherein

R$^1$ is H, alkyl, cycloalkyl, cycloalkylalkyl, phenyl, aralkyl;

R$^2$ is NHR$^3$;

AA$^1$ is OR$^1$, NH$_2$, Val-OR$^1$, Val-NH$_2$, Val-Asn-OR$^1$, Val-Asn-NH$_2$, Val-β-Ala-NH$_2$, Val-β-Ala-OR$^1$, Val-Asn-Thr-OR$^1$, Val-Asn-Thr-ProOR$^1$ (SEQ ID NO: 1), Val-Asn-Thr-pro-Glu-NH$_2$ (SEQ ID NO:2), Asn-OR$^1$, Asn-NH$_2$, Asn-Thr-OR$^1$, Asn-Thr-pro-OR$^1$, Asn-Thr-Pro-Glu-NH$_2$ (SEQ ID NO:3), β-Ala-OR$^1$, β-Ala-NHR$^1$, Trp-OR$^1$, Trp-NH$_2$, Trp-β-Ala-OR$^1$, Trp-NH-R$^1$;

R$^3$ is AA$^2$;

AA$^2$ is R$^4$-Trp, R$^4$-Ile-Trp, R$^4$-Ile-Ile-Trp, R$^4$-Asp-Ile-Ile-Trp (SEQ ID NO:4), R$^4$ (OR$^1$)Asp-Ile-Ile-Trp (SEQ ID NO:5), with the proviso that when AA$^1$ is OR$^1$ or NH$_2$ then AA$^2$ must be at least 3 amino acids;

R$^4$ is H, acetyl, benzoyl, carbobenzyloxy, t-butoxycarbonyl, or a pharmaceutically acceptable salt, thereof.

51. A compound of claim 50 which is N-acetyl-L-α-aspartyl-L-isoleucyl-L-isoleucyl-L-tryptophyl-L-cysteinamide (SEQ ID: NO:21).

52. A compound of claim 50 which is L-isoleucyl-L-isoleucyl-L-tryptophyl-L-cysteinamide (SEQ ID NO:31).

53. A compound of claim 50 which is N-acetyl-L-isoleucyl-L-isoleucyl-L-tryptophyl-L-cysteinylamide (SEQ ID NO:30).

54. A compound of claim 50 which is L-isoleucyl-L-isoleucyl-L-tryptophyl-L-cysteinyl-L-valyl-L-asparagine (SEQ ID NO:29).

55. A compound of claim 50 which is N-acetyl-L-isoleucyl-L-isoleucyl-L-tryptophyl-L-cysteinyl-L-valyl-L-aspargine (SEQ ID NO:25).

56. A compound of claim 50 which is N-acetyl-L-isoleucyl-L-isoleucyl-L-tryptophyl-L-cysteinyl-L-valyl-β-alanine (SEQ ID NO:26).

57. A pharmaceutical composition comprising at least one compound according to claim 50, together with one or more non-toxic pharmaceutically acceptable carriers.

58. A compound of the following formula II

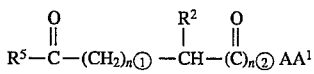

wherein:
- $R^1$ is H, alkyl, cycloalkyl, cycloalkylalkyl, phenyl, aralkyl;
- $R^2$ is $NHR^3$;
- $AA^1$ is Val-$OR^1$, Val-$NH_2$, Val-Asn-$OR^1$, Val-Asn-$NH_2$, Val-β-Ala-$NH_2$, Val-β-Ala-$OR^1$, Val-Asn-Thr-Pro-$OR^1$ (SEQ ID NO:1), Val-Asn-Thr-Pro-$OR^1$, Val-Asn-Thr-Pro-Glu-$NH_2$ (SEQ ID NO:2), Asn-$OR^1$, Asn-N $H_2$, Asn-Thr-$OR^1$, Asn-Thr-pro-$OR^1$, Asn-Thr-Pro-Glu-$NH_2$ (SEQ ID NO:3), β-Ala-$OR^1$, β-Ala-$NHR^1$, Trp-$OR^1$, Trp-$NH_2$, Trp-β-Ala-$OR^1$, Trp-NH-$R^1$;
- $R^3$ is $AA^2$;
- $AA^2$ is $R_4$-Trp, $R^4$-Ile-Trp, $R^4$-Ile-Ile-Trp, $R^4$-Asp-Ile-Ile-Trp (SEQ ID NO:4), $R^4(OR^1)$Asp-Ile-Ile-Trp (SEQ ID NO:5).
- $R^4$ is H, acetyl, benzoyl, carbobenzyloxy, t-butoxycarbonyl;
- $R^5$ is $OR^1$, $NHOR^1$;
- $n①$ is 0, 1, 2;
- $n②$ >is 1;

or a pharmaceutically acceptable salt thereof.

59. A compound of claim 58 which is N-acetyl-L-α-aspartyl-L-isoleucyl-L-isoleucyl-L-tyrptophyl-L-αglutamyl-L-valyl-L-asparaginyl-L-threonyl-L-prolyl-L-α-glutamine (SEQ ID NO:17).

60. A compound of claim 58 which is N-acetyl-L-α-aspartyl-L-isoleucyl-L-isoleucyl-L-tryptophyl-L-αaspartyl-L-asparaginyl-threonyl-L-prolyl-L-α-glutamine (SEQ ID NO:18).

61. A compound of claim 58 which is N-acetyl-L-isoleucyl-L-isoleucyl-L-tryptophyl-L-α-glutamyl-L-valyl-L-asparagine (SEQ ID NO:28).

62. A compound of claim 58 which is N-acetyl-L-isoleucyl-L-isoleucyl-L-tryptophyl-L-α-glutamyl-L-valyl-L-α-alanine (SEQ ID NO:27).

63. A compound of claim 58 which is N-acetyl-L-isoleucyl-L-isoleucyl-L-N-acetyl-L-isoleucyl-L-isoleucyl-N 5-hydroxy-L-glutaminyl-L-valyl-L-asparaginylamide (SEQ ID NO:32).

64. A compound of claim 58 which is N-acetyl-L-isoleucyl-L-isoleucyl-L-tryptophyl-L-α-aspartyl-L-valyl-L-asparagine (SEQ ID NO:23).

65. A compound of claim 58 which is N-acetyl-L-isoleucyl-L-isoleucyl-L-tryptophyl-L-α-aspartyl-L-valyl-β-alanine (SEQ ID NO:24).

66. A compound of claim 58 which is N-acetyl-L-isoleucyl-L-isoleucyl-L-tryptophyl-$N_4$-hydroxy-L-asparaginyl-L-valyl-L-asparaginylamide (SEQ ID NO:33).

67. A pharmaceutical composition comprising at least one compound according to claim 58, together with one or more non-toxic pharmaceutically acceptable carriers.

68. A compound of the following formula VI

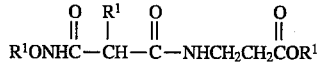

wherein
$R^1$ is H, alkyl, cycloalkyl, cycloalkylalkyl, phenyl, aralkyl; or a pharmaceutically acceptable salt thereof.

69. A compound of claim 68 which is N-[2[(hydroxyamino)carbonyl]- 3-methyl-1-oxobutyl]-β-alanine.

70. A pharmaceutical composition comprising at least one compound according to claim 68, together with one or more non-toxic pharmaceutically acceptable carriers.

71. A method of treating stroke, cardiac arrhythmia, renal ischemic dysfunction, angina, or myocardia infarction, comprising administering, an effective amount of a compound selected from the group consisting of the following Formulae I–VI:

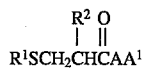

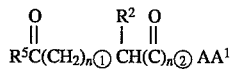

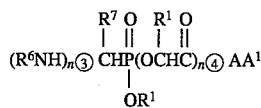

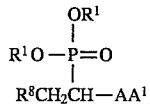

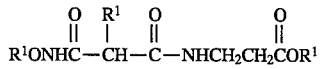

wherein
- $R^1$ is H, alkyl, cycloalkyl, cycloalkylalkyl, phenyl, aralkyl;
- $R^2$ is H, alkyl, phenyl, aralkyl, (3-indolyl)methylene, $NHR^3$;
- $AA^1$ is $OR^1$, $NH_2$, Val-$OR^1$, Val-$NH_2$, Val-Asn-$OR^1$, Val-Asn-$NH_2$, Val-β-Ala-$NH_2$, Val-β-Ala-$OR^1$, Val-Asn-Thr-$OR^1$, Val-Asn-Thr-Pro-$OR^1$(SEQ ID NO:1), Val-Asn-Thr-Pro-Glu-$NH_2$(SEQ ID NO:2), Asn-$OR^1$, Asn-$NH_2$, Asn-Thr-$OR^1$, Asn-Thr-Pro-$OR^1$, Asn-Thr-Pro-Glu-$NH_2$ (SEQ ID NO:3), β-Ala-$OR^1$, β-Ala-$NHR^1$, Trp-$OR^1$, Trp-$NH_2$, Trp-β-Ala-$OR^1$, Trp-NH-$R^1$;
- $R^3$ is H, acetyl, benzoyl, $AA^2$;
- $AA^2$ is $R^4$-Trp, $R^4$-Ile-Trp, $R^4$-Ile-Ile-Trp, $R^4$-Asp-Ile-Ile-Trp (SEQ ID NO:4), $R^4$-$(OR^1)$Asp-Ile-Ile-Trp (SEQ ID NO:5), with the proviso that in formula III $AA^2$ must be at least three amino acids in length;
- $R^4$ is H, acetyl, benzoyl, carbobenzyloxy, t-butoxycarbonyl;
- $R^5$ is $OR^1$, $NHOR^1$;
- $n①$ is 0, 1, 2;
- $n②$ is 0, 1 and when in Formula II $R^2$=$NHR^3$, $n②$ cannot be zero;
- $n③$ =0, 1 and when absent it is replaced by H;
- $n④$ 0, 1;
- $R^6$ is $R^4$ $AA^2$, $R^{4\text{-}Ile}$ $R^4$-Ile-Ile, $R^4$-Asp-Ile-Ile, $R^4$-$(OR^1)$Asp-Ile-Ile;
- $R^7$ is $R^1$, (3-indolyl)methylene;
- $R^8$ is $R^7$, $NHR^6$, or a pharmaceutically acceptable salt thereof.

* * * * *

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /note="C-TERMINAL -OR1, WHEREIN R1 IS H, ALKYL, CYCLOALKYL, CYCLOALKYLALKYL, PHENYL, ARALKYL."

( x i ) SEQUENCE DESCRIPTION: SEQ ID NO:1:

Val Asn Thr Pro
    1

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /note="C-TERMINAL AMIDE ESTER"

( x i ) SEQUENCE DESCRIPTION: SEQ ID NO:2:

Val Asn Thr Pro Glu
1               5

( 2 ) INFORMATION FOR SEQ ID NO:3:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Modified-site
  ( B ) LOCATION: 4
  ( D ) OTHER INFORMATION: /note="C-TERMINAL AMIDE ESTER"

( x i ) SEQUENCE DESCRIPTION: SEQ ID NO:3:

Asn Thr Pro Glu
1

( 2 ) INFORMATION FOR SEQ ID NO:4:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /note="N-TERMINAL R4, WHEREIN R4
        IS H, ACETYL, BENZOYL, CARBOBENZYLOXY,
        T- BUTOXYCARBONYL."

( x i ) SEQUENCE DESCRIPTION: SEQ ID NO:4:

Asp Ile Ile Trp
1

( 2 ) INFORMATION FOR SEQ ID NO:5:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /note="N-TERMINAL R4-(OR1)-,
        WHEREIN R4 IS H, ACETYL, BENZOYL, CARBOBENZYLOXY,
        T- BUTOXYCARBONYL, AND R1 IS H, ALKYL, CYCLOALKYL, ( x i ) SEQUENCE DESCRIPTION: SEQ ID NO:5:

Asp Ile Ile Trp
1

( 2 ) INFORMATION FOR SEQ ID NO:6:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear (i i) MOLECULE TYPE: peptide (i x) FEATURE:
 (A) NAME/KEY: Modified-site
 (B) LOCATION: 1
 (D) OTHER INFORMATION: /note="N-TERMINAL N-ACETYL"

(i x) FEATURE:
 (A) NAME/KEY: Modified-site
 (B) LOCATION: 4
 (D) OTHER INFORMATION: /note="C-TERMINAL AMIDE ESTER"

(x i) SEQUENCE DESCRIPTION: SEQ ID NO:6:

Ile Ile Trp Glu
1

(2) INFORMATION FOR SEQ ID NO:7:

(i) SEQUENCE CHARACTERISTICS:
  (A) LENGTH: 4 amino acids
  (B) TYPE: amino acid
  (C) STRANDEDNESS: single
  (D) TOPOLOGY: linear (i i) MOLECULE TYPE: peptide (i x) FEATURE:
  (A) NAME/KEY: Modified-site
  (B) LOCATION: 1
  (D) OTHER INFORMATION: /note="N-TERMINAL N-ACETYL"

(i x) FEATURE:
  (A) NAME/KEY: Modified-site
  (B) LOCATION: 4
  (D) OTHER INFORMATION: /note="C-TERMINAL AMIDE ESTER"

(x i) SEQUENCE DESCRIPTION: SEQ ID NO:7:

Ile Ile Trp Asp
1

(2) INFORMATION FOR SEQ ID NO:8:

(i) SEQUENCE CHARACTERISTICS:
  (A) LENGTH: 4 amino acids
  (B) TYPE: amino acid
  (C) STRANDEDNESS: single
  (D) TOPOLOGY: linear (i i) MOLECULE TYPE: peptide (i x) FEATURE:
  (A) NAME/KEY: Modified-site
  (B) LOCATION: 1
  (D) OTHER INFORMATION: /note="N-TERMINAL N-ACETYL"

(i x) FEATURE:
  (A) NAME/KEY: Modified-site
  (B) LOCATION: 4
  (D) OTHER INFORMATION: /note="N5-HYDROXY"

(i x) FEATURE:
  (A) NAME/KEY: Modified-site
  (B) LOCATION: 4
  (D) OTHER INFORMATION: /note="C-TERMINAL AMIDE ESTER"

(x i) SEQUENCE DESCRIPTION: SEQ ID NO:8:

Ile Ile Trp Gln
1

(2) INFORMATION FOR SEQ ID NO:9:

(i) SEQUENCE CHARACTERISTICS:
  (A) LENGTH: 4 amino acids (B) TYPE: amino acid
        (C) STRANDEDNESS: single
        (D) TOPOLOGY: linear ( i i ) MOLECULE TYPE: peptide ( i x ) FEATURE:
        (A) NAME/KEY: Modified-site
        (B) LOCATION: 1
        (D) OTHER INFORMATION: /note="N-TERMINAL N-ACETYL"

( i x ) FEATURE:
        (A) NAME/KEY: Modified-site
        (B) LOCATION: 4
        (D) OTHER INFORMATION: /note="N4-HYDROXY"

( i x ) FEATURE:
        (A) NAME/KEY: Modified-site
        (B) LOCATION: 4
        (D) OTHER INFORMATION: /note="C-TERMINAL AMIDE ESTER"

( x i ) SEQUENCE DESCRIPTION: SEQ ID NO:9:

Ile Ile Trp Asn
1

( 2 ) INFORMATION FOR SEQ ID NO:10:

( i ) SEQUENCE CHARACTERISTICS:
        (A) LENGTH: 4 amino acids
        (B) TYPE: amino acid
        (C) STRANDEDNESS: single
        (D) TOPOLOGY: linear ( i i ) MOLECULE TYPE: peptide ( i x ) FEATURE:
        (A) NAME/KEY: Modified-site
        (B) LOCATION: 1
        (D) OTHER INFORMATION: /note="N-TERMINAL N-ACETYL"

( i x ) FEATURE:
        (A) NAME/KEY: Modified-site
        (B) LOCATION: 4
        (D) OTHER INFORMATION: /note="C-TERMINAL AMIDE ESTER"

( i x ) FEATURE:
        (A) NAME/KEY: Modified-site
        (B) LOCATION: 4
        (D) OTHER INFORMATION: /note="N1-(2-METHYLETHYL)"

( x i ) SEQUENCE DESCRIPTION: SEQ ID NO:10:

Ile Ile Trp Glu
    1

( 2 ) INFORMATION FOR SEQ ID NO:11:

( i ) SEQUENCE CHARACTERISTICS:
        (A) LENGTH: 4 amino acids
        (B) TYPE: amino acid
        (C) STRANDEDNESS: single
        (D) TOPOLOGY: linear ( i i ) MOLECULE TYPE: peptide ( i x ) FEATURE:
        (A) NAME/KEY: Modified-site
        (B) LOCATION: 1
        (D) OTHER INFORMATION: /note="N-TERMINAL N-ACETYL"

( i x ) FEATURE:
        (A) NAME/KEY: Modified-site
        (B) LOCATION: 4
        (D) OTHER INFORMATION: /note="N5-HYDROXY"

( i x ) FEATURE:
        (A) NAME/KEY: Modified-site (B) LOCATION: 4
(D) OTHER INFORMATION: /note="C-TERMINAL AMIDE ESTER"

(ix) FEATURE:
(A) NAME/KEY: Modified-site
(B) LOCATION: 4
(D) OTHER INFORMATION: /note="N1-(2-METHYLETHYL)"

(xi) SEQUENCE DESCRIPTION: SEQ ID NO:11:

Ile Ile Trp Gln
1

(2) INFORMATION FOR SEQ ID NO:12:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="N-TERMINAL N-ACETYL"

(ix) FEATURE:
(A) NAME/KEY: Modified-site
(B) LOCATION: 4
(D) OTHER INFORMATION: /note="C-TERMINAL AMIDE ESTER"

(ix) FEATURE:
(A) NAME/KEY: Modified-site
(B) LOCATION: 4
(D) OTHER INFORMATION: /note="N1-(2-METHYLETHYL)"

(xi) SEQUENCE DESCRIPTION: SEQ ID NO:12:

Ile Ile Trp Asp
1

(2) INFORMATION FOR SEQ ID NO:13:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="N-TERMINAL N-ACETYL"

(ix) FEATURE:
(A) NAME/KEY: Modified-site
(B) LOCATION: 4
(D) OTHER INFORMATION: /note="N4-HYDROXY"

(ix) FEATURE:
(A) NAME/KEY: Modified-site
(B) LOCATION: 4
(D) OTHER INFORMATION: /note="C-TERMINAL AMIDE ESTER"

(ix) FEATURE:
(A) NAME/KEY: Modified-site
(B) LOCATION: 4
(D) OTHER INFORMATION: /note="N1-(2-METHYLETHYL)"

(xi) SEQUENCE DESCRIPTION: SEQ ID NO:13:

Ile Ile Trp Asn
1

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Modified-site
        ( B ) LOCATION: 1
        ( D ) OTHER INFORMATION: /note="N-TERMINAL N-ACETYL"

( x i ) SEQUENCE DESCRIPTION: SEQ ID NO:14:

```
Asp  Val  Asn  Thr  Pro  Gln
1                   5
```

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="N-TERMINAL N-ACETYL"

( x i ) SEQUENCE DESCRIPTION: SEQ ID NO:15:

```
Glu  Val  Asn  Thr  Pro  Gln
1                   5
```

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="N-TERMINAL N-ACETYL"

( i x ) FEATURE:
        ( A ) NAME/KEY: Modified-site
        ( B ) LOCATION: 6
        ( D ) OTHER INFORMATION: /note="C-TERMINAL AMIDE ESTER"

( x i ) SEQUENCE DESCRIPTION: SEQ ID NO:16:

```
Cys  Val  Asn  Thr  Pro  Gln
1                   5
```

( 2 ) INFORMATION FOR SEQ ID NO:17:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:

( A ) NAME/KEY: Modified-site
( B ) LOCATION: 1
( D ) OTHER INFORMATION: /note="N-TERMINAL N-ACETYL"

( x i ) SEQUENCE DESCRIPTION: SEQ ID NO:17:

```
Asp  Ile  Ile  Trp  Glu  Val  Asn  Thr  Pro  Gln
1                   5                        10
```

( 2 ) INFORMATION FOR SEQ ID NO:18:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="N-TERMINAL N-ACETYL"

( x i ) SEQUENCE DESCRIPTION: SEQ ID NO:18:

```
Asp  Ile  Ile  Trp  Asp  Val  Asn  Thr  Pro  Gln
1                   5                        10
```

( 2 ) INFORMATION FOR SEQ ID NO:19:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="N-TERMINAL N-ACETYL"

( i x ) FEATURE:
( A ) NAME/KEY: Modified-site
( B ) LOCATION: 5
( D ) OTHER INFORMATION: /note="C-TERMINAL AMIDE ESTER"

( x i ) SEQUENCE DESCRIPTION: SEQ ID NO:19:

```
Asp  Ile  Ile  Trp  Asp
1                   5
```

( 2 ) INFORMATION FOR SEQ ID NO:20:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="N-TERMINAL N-ACETYL"

( i x ) FEATURE:
( A ) NAME/KEY: Modified-site
( B ) LOCATION: 5
( D ) OTHER INFORMATION: /note="C-TERMINAL AMIDE ESTER"

( x i ) SEQUENCE DESCRIPTION: SEQ ID NO:20:

```
Asp  Ile  Ile  Trp  Glu
```

(2) INFORMATION FOR SEQ ID NO:21:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="N-TERMINAL N-ACETYL"

(ix) FEATURE:
        (A) NAME/KEY: Modified-site
        (B) LOCATION: 5
        (D) OTHER INFORMATION: /note="C-TERMINAL AMIDE ESTER"

(xi) SEQUENCE DESCRIPTION: SEQ ID NO:21:

Asp Ile Ile Trp Cys
1               5

(2) INFORMATION FOR SEQ ID NO:22:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="N-TERMINAL N-ACETYL"

(xi) SEQUENCE DESCRIPTION: SEQ ID NO:22:

Asp Ile Ile Trp
1

(2) INFORMATION FOR SEQ ID NO:23:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="N-TERMINAL N-ACETYL"

(xi) SEQUENCE DESCRIPTION: SEQ ID NO:23:

Ile Ile Trp Asp Val Asn
1               5

(2) INFORMATION FOR SEQ ID NO:24:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide ( i x ) FEATURE:
    ( A ) NAME/KEY: Modified-site
    ( B ) LOCATION: 1
    ( D ) OTHER INFORMATION: /note="N-TERMINAL N-ACETYL"

( i x ) FEATURE:
    ( A ) NAME/KEY: Modified-site
    ( B ) LOCATION: 6
    ( D ) OTHER INFORMATION: /note="bAla"

( x i ) SEQUENCE DESCRIPTION: SEQ ID NO:24:

Ile Ile Trp Asp Val Xaa
1              5

( 2 ) INFORMATION FOR SEQ ID NO:25:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="N-TERMINAL N-ACETYL"

( x i ) SEQUENCE DESCRIPTION: SEQ ID NO:25:

Ile Ile Trp Cys Val Asn
1              5

( 2 ) INFORMATION FOR SEQ ID NO:26:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="N-TERMINAL N-ACETYL"

( i x ) FEATURE:
    ( A ) NAME/KEY: Modified-site
    ( B ) LOCATION: 6
    ( D ) OTHER INFORMATION: /note="bAla"

( x i ) SEQUENCE DESCRIPTION: SEQ ID NO:26:

Ile Ile Trp Cys Val Xaa
1              5

( 2 ) INFORMATION FOR SEQ ID NO:27:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="N-TERMINAL N-ACETYL"

( i x ) FEATURE:

(A) NAME/KEY: Modified-site
(B) LOCATION: 6
(D) OTHER INFORMATION: /note="bAla"

(xi) SEQUENCE DESCRIPTION: SEQ ID NO:27:

Ile Ile Trp Glu Val Xaa
1               5

(2) INFORMATION FOR SEQ ID NO:28:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="N-TERMINAL N-ACETYL"

(xi) SEQUENCE DESCRIPTION: SEQ ID NO:28:

Ile Ile Trp Glu Val Asn
1               5

(2) INFORMATION FOR SEQ ID NO:29:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:29:

Ile Ile Trp Cys Val Asn
1               5

(2) INFORMATION FOR SEQ ID NO:30:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="N-TERMINAL N-ACETYL"

(ix) FEATURE:
(A) NAME/KEY: Modified-site
(B) LOCATION: 4
(D) OTHER INFORMATION: /note="C-TERMINAL AMIDE ESTER"

(xi) SEQUENCE DESCRIPTION: SEQ ID NO:30:

Ile Ile Trp Cys
1

(2) INFORMATION FOR SEQ ID NO:31:

(i) SEQUENCE CHARACTERISTICS:
(A) LENGTH: 4 amino acids
(B) TYPE: amino acid
(C) STRANDEDNESS: single
(D) TOPOLOGY: linear ( i i ) MOLECULE TYPE: peptide ( i x ) FEATURE:
    ( A ) NAME/KEY: Modified-site
    ( B ) LOCATION: 4
    ( D ) OTHER INFORMATION: /note="C-TERMINAL AMIDE ESTER"

( x i ) SEQUENCE DESCRIPTION: SEQ ID NO:31:

Ile Ile Trp Cys
1

( 2 ) INFORMATION FOR SEQ ID NO:32:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="N-TERMINAL N-ACETYL"

( i x ) FEATURE:
        ( A ) NAME/KEY: Modified-site
        ( B ) LOCATION: 4
        ( D ) OTHER INFORMATION: /note="N5-HYDROXY"

( i x ) FEATURE:
        ( A ) NAME/KEY: Modified-site
        ( B ) LOCATION: 6
        ( D ) OTHER INFORMATION: /note="C-TERMINAL AMIDE ESTER"

( x i ) SEQUENCE DESCRIPTION: SEQ ID NO:32:

Ile Ile Trp Gln Val Asn
1               5

( 2 ) INFORMATION FOR SEQ ID NO:33:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="N-TERMINAL N-ACETYL"

( i x ) FEATURE:
        ( A ) NAME/KEY: Modified-site
        ( B ) LOCATION: 4
        ( D ) OTHER INFORMATION: /note="N4-HYDROXY"

( i x ) FEATURE:
        ( A ) NAME/KEY: Modified-site
        ( B ) LOCATION: 6
        ( D ) OTHER INFORMATION: /note="C-TERMINAL AMIDE ESTER"

( x i ) SEQUENCE DESCRIPTION: SEQ ID NO:33:

Ile Ile Trp Asn Val Asn
1               5